(12) United States Patent
Wagner et al.

(10) Patent No.: US 8,541,560 B2
(45) Date of Patent: Sep. 24, 2013

(54) POLYPEPTIDES COMPRISING FAS ACTIVATION AND NKG2D-LIGAND DOMAINS

(75) Inventors: Thomas E. Wagner, Greenville, SC (US); Yanzhang Wei, Greer, SC (US)

(73) Assignee: Thomas E. Wagner, Greenville, SC (US)

( * ) Notice: Subject to any disclaimer, the term of this patent is extended or adjusted under 35 U.S.C. 154(b) by 321 days.

(21) Appl. No.: 12/826,544

(22) Filed: Jun. 29, 2010

(65) Prior Publication Data

US 2010/0284975 A1 Nov. 11, 2010

Related U.S. Application Data

(62) Division of application No. 11/945,747, filed on Nov. 27, 2007, now Pat. No. 7,777,004.

(60) Provisional application No. 60/907,586, filed on Apr. 10, 2007, provisional application No. 60/861,242, filed on Nov. 28, 2006.

(51) Int. Cl.
*C07H 21/02* (2006.01)

(52) U.S. Cl.
USPC ........................................ 536/23.1; 514/44 R

(58) Field of Classification Search
None
See application file for complete search history.

(56) References Cited

U.S. PATENT DOCUMENTS

2004/0192631 A1 9/2004 Xiang et al.

FOREIGN PATENT DOCUMENTS

WO WO 01/00854 1/2001

OTHER PUBLICATIONS

Aileen Houston et al., The FAS signaling pathway and its role in the pathogenesis of cancer, www.sciencedirect.com, Current Opinion Pharmacology 2004, 4:321-326, Elsevier.
Apoptosis Induced by FAS Ligand Download, http://www.genomicobject.net/member3/GONET/apoptosis.html, p. 1-5. Internet date Oct. 3, 2006.
Routes JM et al., Adenovirus serotype 5 E1A sensitizes tumor cells to NKG2D-dependent NK cell lysis and tumor rejection. http://www.ncbi.nlm.nih.gov/entrez/query.fcgi?db=pubmed&cmd=Retrieve &dopt=Abstr . . . , p. 1, Oct. 9, 2006.
Nicholas Wade, Virus Linked to Colds May Cure Cancer, Scientists Say, The New York Times, Oct. 9, 2006. Health Section, gages 1 & 2. http://query.nytimes.com, Oct. 9, 2006.
Sumia Ali et al., Combined Immunostimulatio and Conditional Cytotoxic Gene Therapy Provide Long-term Survival in a Large Glioma Model. Research Article, Cancer Res 2005; 65(16). Aug. 15, 2005, www.accrjournals.org, pp. 7194-7204.
Heise C, et al. Onyx-015, an E1B gene-attenuated adenovirus, causes tumor-specific cytolysis and antitumoral efficacy that can be augmented by standard chemotherapeutic agents. http://www.ncbi.nlm.nih.gov/entrez/query.fcgi?db=pubmed&cmd=Retrieve&dopt= Abstr . . . , p. Oct. 9, 2006.
Rothmann T. et al. Replication ONYX-015, a potential anticancer adenovirus, is independent of p53 status in tumor cells. http://www.ncbi.nlm.nih.gov/entrez/query.fcgi?db=pubmed&cmd=Retrieve &dopt=Abstr . . . , p. 1, Oct. 9, 2006.
Heise CC, et al. Efficacy of a replication-competent adenovirus (ONYX-015) following intratumoral injection: intratumoral spread and distribution effects. http://www.ncbi.nlm.nih.gov/entrez/query.fcgi?db=pubmed&cmd=Retrieve&dopt=Abstr . . . , p. 1, Oct. 9, 2006.
Ries SJ. Elucidation of the molecular mechanism underlying tumor-selective replication of the oncolytic adenovirus mutant ONYX-015. http://www.ncbi.nlm.nih.gov/entrez/query.fcgi?db= pubmed&cmd=Retrieve&dopt=Abstr . . . , p. 1, Oct. 9, 2006.
Stefan Bauer et al. Activation of NK Cells and T Cells by NKG2D, a Receptor for Stress-Inducible MICA, www.sciencemag.org, Science vol. 285 Jul. 30, 1999, pp. 727-729.
Astrid Krmpotic et al. NK cell activation through the NKG2D ligand MULT-1 is selectively prevented by the glycoprotein encoded by mouse cytomegalovirus gene m145, The Journal of Experimental Medicine, The Rockefeller University Press vol. 201, No. 2, Jan. 17, 2005 211-220, downloaded from www.jem.org on Oct. 2, 2006.
Andreas Diefenbach et al. Selective associations with signaling proteins determine stimulatory versus costimulatory activity of NKG2D, 2002 Nature Publishing Group http://wvvw.nature.com/natureimmunology . vol. 3 No. 12, Dec. 2002, pp. 1142-1149.
Leonidas N. Carayannopoulos et al., Cutting Edge: Murine UL 16-Binding Protein-Like Transcript 1: A Newly Described Transcript Encoding a High-Affinity Ligand for Murine NKG2D, 2002 by The American Association of Immunologists, Inc., 002-1767/02, The Journal of Immunology, pp. 4079-4083.
Seiamak Bahram et al., MIC and other NKG2D ligands: from none to too many, www.sciencedirect.com, Current Opinion in Immunology 2005, 17:505-509, Elsevier.
E. Backstrom et al., Activation of Natural Killer Cells: Underlying Molecular Mechanisms Revealed, 2004 Blackwell Publishing Ltd. Scandinavian Journal of Immunology 60, pp. 14-22.
Andreas Diefenbach et al., A novel ligand ofr the NKG2D receptor activates NK cells and macrophages and induces tumor immunity, Eur. J. Immunol. 2003, 33: 381-391, 2003 Wiley-VCH Verlag GmbH & Co. KGaA, Weinheim 0014-2980/03/0202-381.
David H. Rault, Roles of the NKG2D Immunoreceptor and its Ligands, Nature Reviews, Immunology, vol. 3, Oct. 2003, pp. 781-790.
Andreas Diefenbach et al., Ligands for the murine NKG2D receptor: expression by tumor cells and activation of NK cells and macrophages, 2000 Nature America Inc., http://immunol.nature.com, Aug. 2000, vol. 1, No. 2, pp. 119-126.
Coudert et al., "The Role of the NKG2D Receptor for Tumor Immunity," *Seminars in Cancer Biology* 16, pp. 333-343 (2006).
Busche et al., "Natural Killer Cell-Mediated Rejection of Experimental Human Lung Cancer by Genetic Overexpression of Major Histocompatibility Complex Class I Chain-Related Gene A," *Human Gene Therapy 17*, pp. 135-146 (2006).
International Search Report for PCT/US2007/085631, dated Sep. 26, 2008, 3 pgs.
Written Opinion for for PCT/US2007/085631, dated Sep. 26, 2008, 8 pgs.

*Primary Examiner* — Mark Halvorson
(74) *Attorney, Agent, or Firm* — Foley & Lardner LLP

(57) ABSTRACT

The present invention is drawn to fusion proteins comprising (a) a ligand for an NK receptor and (b) a Fas activation domain, and to nucleic acids encoding such fusion proteins. The invention also includes methods of making and using such proteins and nucleic acids, including their use in preventing or treating cancer.

9 Claims, 9 Drawing Sheets

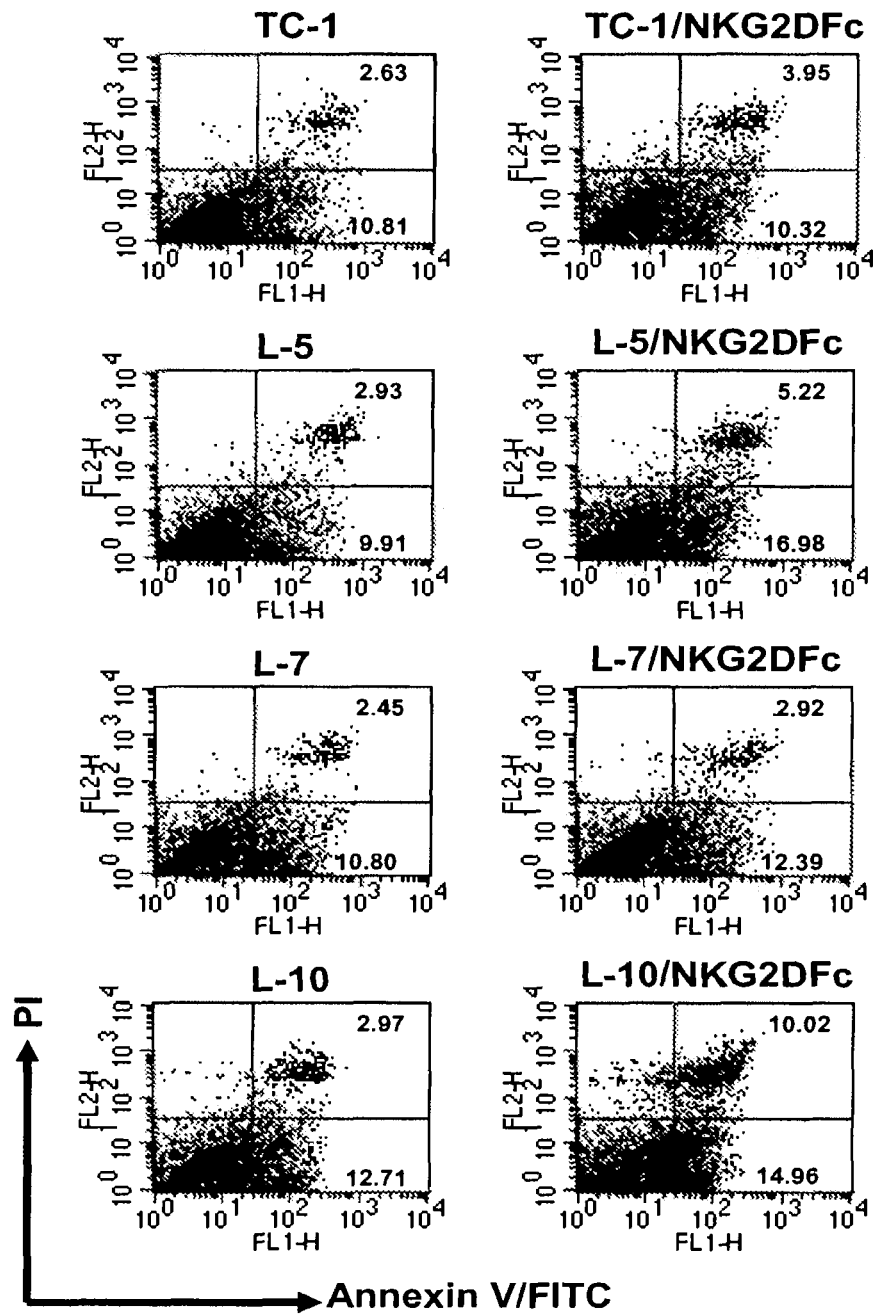

Figure 3B, 3C, and 3D
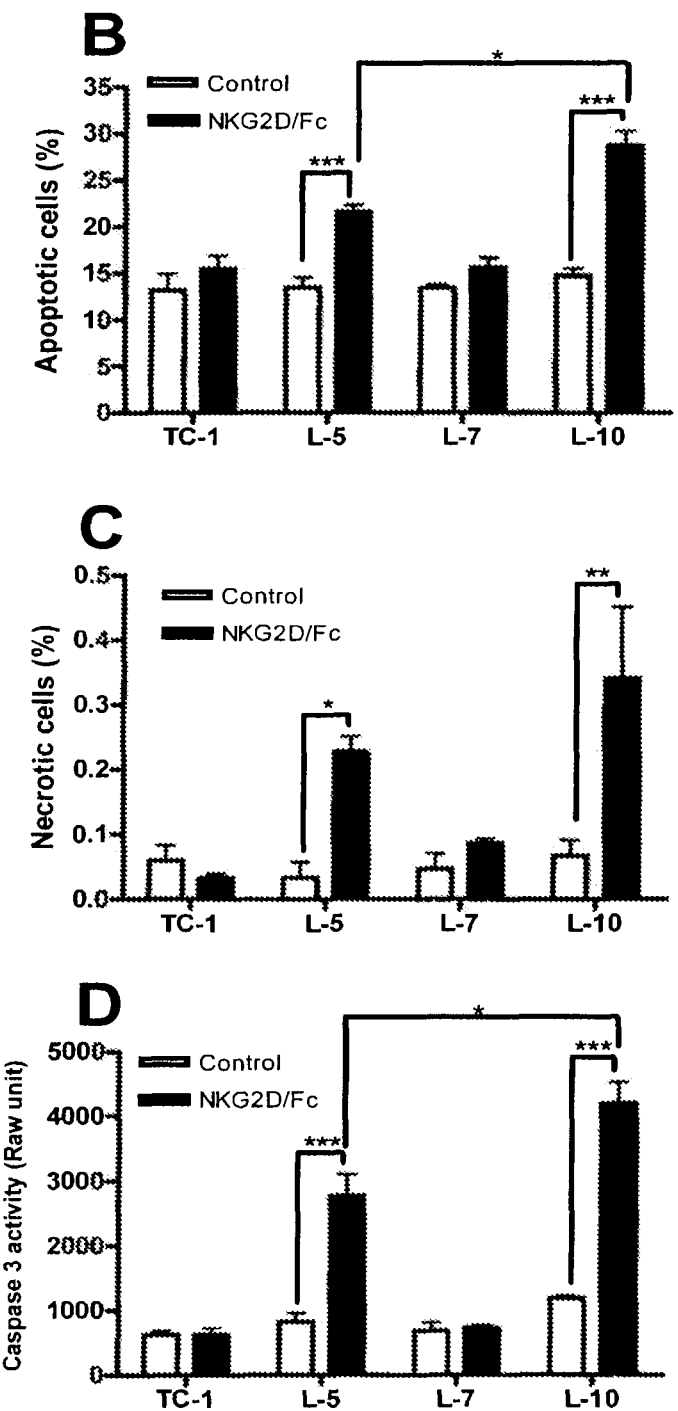

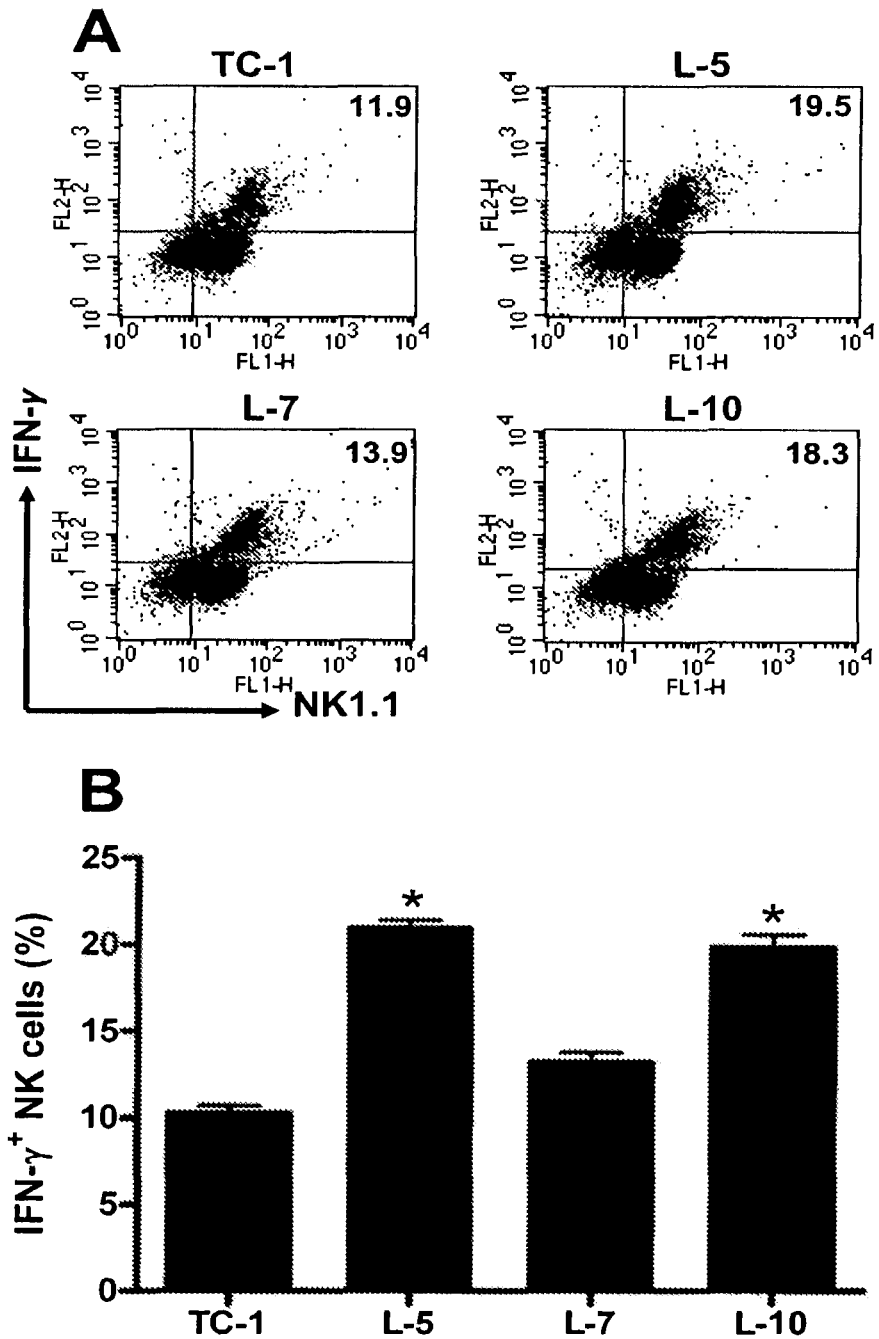
Figure 4A,B

SEQUENCE LISTING

```
<160> NUMBER OF SEQ ID NOS: 10

<210> SEQ ID NO 1
<211> LENGTH: 334
<212> TYPE: PRT
<213> ORGANISM: Mus musculus

<400> SEQUENCE: 1

Met Glu Leu Thr Ala Ser Asn Lys Val Leu Ser Cys Cys Leu Ser Leu
 1               5                  10                  15

Leu Cys Leu Leu Ser Val Cys Leu Cys Pro Arg Ile Glu Glu Thr Ala
            20                  25                  30

Ser Leu Cys Asn Ile Tyr Lys Val Asn Arg Ser Glu Ser Gly Gln His
        35                  40                  45
```

```
Ser His Glu Val Gln Gly Leu Leu Asn Arg Gln Pro Leu Phe Val Tyr
            50                  55                  60

Lys Asp Lys Lys Cys His Ala Ile Gly Ala His Arg Asn Ser Met Asn
 65                  70                  75                  80

Ala Thr Lys Ile Cys Glu Lys Glu Val Asp Thr Leu Lys Asp Gly Ile
                 85                  90                  95

Asp Ile Phe Lys Gly Leu Leu His Ile Val Gln Glu Thr Asn Thr
                100                 105                 110

Thr Gly Lys Pro Leu Thr Leu Gln Ala Glu Val Cys Gly Gln Tyr Glu
            115                 120                 125

Val Asp Lys His Phe Thr Gly Tyr Ala Ile Val Ser Leu Asn Gly Lys
        130                 135                 140

Asn Ile Phe Arg Val Asp Thr Ser Thr Gly Asn Trp Thr Gln Leu Asp
145                 150                 155                 160

His Glu Phe Glu Lys Phe Ile Glu Met Cys Lys Glu Asp Lys Val Leu
                165                 170                 175

Ala Ala Phe Leu Lys Lys Thr Thr Glu Gly Asp Cys Arg Thr Trp Leu
                180                 185                 190

Asp Glu Leu Met Leu His Trp Lys Glu His Leu Glu Pro Ala Gly Ser
            195                 200                 205

Phe Ser Thr Leu Met Ile Ile Leu Cys Val Ile Ala Ile Ala Phe Leu
210                 215                 220

Gly Leu Ile Phe Gly Val Ser Cys Lys Leu Arg His Leu Arg Thr Lys
225                 230                 235                 240

Lys Ile Gly Leu Gln Ser Ser Pro Pro Leu Leu Asp Asp Ser Leu
                245                 250                 255

Thr Val Pro Thr Ser Pro Gln Ser Ser Val Cys Gly Thr Met Ile Gln
                260                 265                 270

Cys Leu Cys Pro Arg Lys Leu Lys Ser Pro Val Phe Met Gln Ile Asp
            275                 280                 285

Leu Gln Ser Ser Ala Pro Pro Leu Leu Asp Asp Ser Leu Thr Val Pro
        290                 295                 300

Glu Thr Cys Ser Val Lys Lys Glu Asp Glu Phe Pro Thr Ala Ser Gln
305                 310                 315                 320

Asn Ser Val Leu Leu Thr Ser Asp Asp Ile Asp Gly Ile Pro
                325                 330

<210> SEQ ID NO 2
<211> LENGTH: 327
<212> TYPE: PRT
<213> ORGANISM: Mus musculus

<400> SEQUENCE: 2

Met Leu Trp Ile Trp Ala Val Leu Pro Leu Val Leu Ala Gly Ser Gln
  1               5                  10                  15

Leu Arg Val His Thr Gln Gly Thr Asn Ser Ile Ser Glu Ser Leu Lys
                 20                  25                  30

Leu Arg Arg Arg Val Arg Glu Thr Asp Lys Asn Cys Ser Glu Gly Leu
             35                  40                  45

Tyr Gln Gly Gly Pro Phe Cys Cys Gln Pro Cys Gln Pro Gly Lys Lys
         50                  55                  60

Lys Val Glu Asp Cys Lys Met Asn Gly Gly Thr Pro Thr Cys Ala Pro
 65                  70                  75                  80

Cys Thr Glu Gly Lys Glu Tyr Met Asp Lys Asn His Tyr Ala Asp Lys
                 85                  90                  95
```

```
Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Leu Trp Leu Leu Thr Ile Leu
                165                 170                 175

Val Leu Leu Ile Pro Leu Val Phe Ile Tyr Arg Lys Tyr Arg Lys Arg
            180                 185                 190

Lys Cys Trp Lys Arg Arg Gln Asp Asp Pro Glu Ser Arg Thr Ser Ser
        195                 200                 205

Arg Glu Thr Ile Pro Met Asn Ala Ser Asn Leu Ser Leu Ser Lys Tyr
    210                 215                 220

Ile Pro Arg Ile Ala Glu Asp Met Thr Ile Gln Glu Ala Lys Lys Phe
225                 230                 235                 240

Ala Arg Glu Asn Asn Ile Lys Glu Gly Lys Ile Asp Glu Ile Met His
                245                 250                 255

Asp Ser Ile Gln Asp Thr Ala Glu Gln Lys Val Gln Leu Leu Leu Cys
            260                 265                 270

Trp Tyr Gln Ser His Gly Lys Ser Asp Ala Tyr Gln Asp Leu Ile Lys
        275                 280                 285

Gly Leu Lys Lys Ala Glu Cys Arg Arg Thr Leu Asp Lys Phe Gln Asp
    290                 295                 300

Met Val Gln Lys Asp Leu Gly Lys Ser Thr Pro Asp Thr Gly Asn Glu
305                 310                 315                 320

Asn Glu Gly Gln Cys Leu Glu
                325

<210> SEQ ID NO 3
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Glu Leu Thr Ala Ser Asn Lys Val Leu Ser Cys Cys Leu Ser Leu
  1               5                  10                  15

Leu Cys Leu Leu Ser Val Cys Leu Cys Pro Arg Ile Glu Glu Thr Ala
             20                  25                  30

Ser Leu Cys Asn Ile Tyr Lys Val Asn Arg Ser Glu Ser Gly Gln His
         35                  40                  45

Ser His Glu Val Gln Gly Leu Leu Asn Arg Gln Pro Leu Phe Val Tyr
     50                  55                  60

Lys Asp Lys Lys Cys His Ala Ile Gly Ala His Arg Asn Ser Met Asn
 65                  70                  75                  80

Ala Thr Lys Ile Cys Glu Lys Glu Val Asp Thr Leu Lys Asp Gly Ile
             85                  90                  95

Asp Ile Phe Lys Gly Leu Leu Leu His Ile Val Gln Glu Thr Asn Thr
            100                 105                 110

Thr Gly Lys Pro Leu Thr Leu Gln Ala Glu Val Cys Gly Gln Tyr Glu
        115                 120                 125
```

```
Val Asp Lys His Phe Thr Gly Tyr Ala Ile Val Ser Leu Asn Gly Lys
    130                 135                 140

Asn Ile Phe Arg Val Asp Thr Ser Thr Gly Asn Trp Thr Gln Leu Asp
145                 150                 155                 160

His Glu Phe Glu Lys Phe Ile Glu Met Cys Lys Glu Asp Lys Val Leu
                165                 170                 175

Ala Ala Phe Leu Lys Lys Thr Thr Glu Gly Asp Cys Arg Thr Trp Leu
                180                 185                 190

Asp Glu Leu Met Leu His Trp Lys Glu His Leu Glu Pro Ala Gly Ser
                195                 200                 205

Phe Ser Thr Gly Ser Pro Arg Asn Arg Leu Trp Leu Leu Thr Ile Leu
    210                 215                 220

Val Leu Leu Ile Pro Leu Val Phe Ile Tyr Arg Lys Tyr Arg Lys Arg
225                 230                 235                 240

Lys Cys Trp Lys Arg Arg Gln Asp Asp Pro Glu Ser Arg Thr Ser Ser
                245                 250                 255

Arg Glu Thr Ile Pro Met Asn Ala Ser Asn Leu Ser Leu Ser Lys Tyr
                260                 265                 270

Ile Pro Arg Ile Ala Glu Asp Met Thr Ile Gln Glu Ala Lys Lys Phe
                275                 280                 285

Ala Arg Glu Asn Asn Ile Lys Glu Gly Lys Ile Asp Glu Ile Met His
    290                 295                 300

Asp Ser Ile Gln Asp Thr Ala Glu Gln Lys Val Gln Leu Leu Leu Cys
305                 310                 315                 320

Trp Tyr Gln Ser His Gly Lys Ser Asp Ala Tyr Gln Asp Leu Ile Lys
                325                 330                 335

Gly Leu Lys Lys Ala Glu Cys Arg Arg Thr Leu Asp Lys Phe Gln Asp
                340                 345                 350

Met Val Gln Lys Asp Leu Gly Lys Ser Thr Pro Asp Thr Gly Asn Glu
                355                 360                 365

Asn Glu Gly Gln Cys Leu Glu
    370                 375

<210> SEQ ID NO 4
<211> LENGTH: 1140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
aagcttatgg agctgactgc cagtaacaag gtcctttcct gctgcttgtc cctgctgtgc      60
ctgctgtctg tctgtctgtg tccaaggata gaagagactg cttctctttg taacatttac     120
aaggttaaca ggtcagagtc tggacaacat agtcatgaag ttcaaggcct actcaacaga     180
cagcctcttt ttgtctacaa ggataaaaag tgtcatgcca ttggtgctca taggaacagc     240
atgaatgcta caaagatctg tgaaaaagag gttgacactc tgaaagatgg aattgacatt     300
ttcaaaggtc tgctgcttca catagtgcag agactaacaa caaccggaaa gccccctcact    360 ctgcaggctg aggtgtgtgg ccagtatgaa gtagacaaac atttcacagg atacgccatt     420
gttagcctca atggaaagaa tatattccgt gttgacacaa gcactggcaa ctggacccaa     480
ctggatcatg aattcgagaa gtttatagaa atgtgcaagg aagacaaggt tttagctgcc     540 ttttttaaaga agactacaga gggcgactgc aggacctggc ttgatgagct catgttgcac     600
```

-continued

```
tggaaagaac atctggagcc tgcaggatct ttcagtaccg atcccccag aaatcgccta    660 tggttgttga ccatccttgt tttgttaatt ccacttgtat ttatatatcg aaagtaccgg    720
aaaagaaagt gctggaaaag gagacaggat gaccctgaat ctagaacctc cagtcgtgaa    780
accataccaa tgaatgcctc aaatcttagc ttgagtaaat acatcccgag aattgctgaa    840
gacatgacaa tccaggaagc taaaaaattt gctcgagaaa ataacatcaa ggagggcaag    900
atagatgaga tcatgcatga cagcatccaa gacacagctg agcagaaagt ccagctgctc    960
ctgtgctggt accaatctca tgggaagagt gatgcatatc aagatttaat caagggtctc   1020
aaaaaagccg aatgtcgcag aaccttagat aaatttcagg acatggtcca gaaggacctt   1080
ggaaaatcaa ccccagacac tggaaatgaa aatgaaggac aatgtctgga gtgagaattc   1140
```

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccaagctta tggagctgac tgccagtaac aaggtcc                              37

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgggatccgg tactgaaaga tcctgcaggc tccag                                35

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgggatcccc cagaaatcgc ctatggttgt tgttgacc                             38

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggaattctc actccagaca ttgtccttca ttttc                                35

<210> SEQ ID NO 9
<211> LENGTH: 3696
<212> TYPE: DNA
<213> ORGANISM: Mus musculus

<400> SEQUENCE: 9
ggcaaagcac tggagacaga ctgcaggggc tgcggagctg ctctgaaagg atctggagaa     60

```
agggcacta gaagttgctt ttgacaagat cgggaggagg aattgccttg atcccccagc      120
caaggttcaa aaactttctg tggtcaggac cattatcagg aagtgatcaa gatcgtccct    180 cccttttcaga cagttaaaat cgtgcctttg ccgccagag tctagagaag cagctatgga    240
gctgactgcc agtaacaagg tcctttcctg ctgcttgtcc ctgctgtgcc tgctgtctgt    300
ctgtctgtgt ccaaggatag aagagactgc ttctctttgt aacatttaca aggttaacag    360
gtcagagtct ggacaacata gtcatgaagt tcaaggccta ctcaacagac agcctctttt    420
tgtctacaag gataaaaagt gtcatgccat tggtgctcat aggaacagca tgaatgctac    480
aaagatctgt gaaaagagg ttgacactct gaaagatgga attgacattt tcaaaggtct     540
gctgcttcac atagtgcagg agactaacac aaccggaaag cccctcactc tgcaggctga    600
ggtgtgtggc cagtatgaag tagacaaaca tttcacagga tacgccattg ttagcctcaa    660
tggaaagaat atattccgtg ttgacacaag cactggcaac tggacccaac tggatcatga    720
attcgagaag tttatagaaa tgtgcaagga agacaaggtt ttagctgcct ttttaaagaa    780
gactacagag ggcgactgca ggacctggct tgatgagctc atgttgcact ggaaagaaca    840
tctggagcct gcaggatctt tcagtacctt gatgattatt ctatgcgtga ttgcaattgc    900 cttttctcgga ttgatcttcg gagtctcttg taaattaaga catttacgta caaaaaagat    960
tggcctgcag tcctcaccac cacctctctt ggatgactct ttgacagtgc ctacttcacc    1020
acaatccagt gtatgtggaa ctatgattca atgtctctgt cctcggaagt tgaagtcacc    1080
tgtgtttatg cagattgatc tgcagtcctc agcaccacct ctgttggatg actctttgac    1140
agtgcctgag acgtgttcag taaagaaaga agatgaattt ccgacagcat ctcagaattc    1200
tgtgctgttg acttcagacg atattgatgg gatcccatga gactgatggc cgacagagcc    1260
tcacgcacca gggcatcaga gtgcactagg ctgttgccac caggggcttc ctcttgctct    1320
gttcctttcc tttctcattc ttacatgata gtgctgtgga gatcaagcag ggcatggctc    1380
taagtttctt ctcactgtgc aaaaacaatg atttgtcctg agtgattcca ttttacaagc    1440
agcacttggc tcccttctga gtgcaatgca gacattggag gacagggcac cttaatttaa    1500
acatagatac atgtcagcca ggtaccatcc atgatgcagg tgttgataat taacttaatc    1560
cccaaggtaa aaaatatgc ctcccatgca cttatcaaaa tagatttgaa gtcatgaaca    1620
catgtgcatc tcaaattata tcagagaact aggtctgaga atttatctca ccctcacctg    1680
gtcccctaaa gaagccacct agccctgcaa tgctcatggc ccccacaaac ttgcccctgt    1740
ctgtttgtgt gtcaaggaac cttcagacag aggactcctg gccatcttaa ggcttcagct    1800
ccatccacaa tgctaaagcc tcctgcttga aacgctgtct gacagttcat ctgctgctcc    1860
atgttaatgt gggtctgcat ctcacctgct ggatcctggg gtcctgcacc tcacctctac    1920
agttcactca gtcctgacgc ctggtgcagc ccctgcagcc ctgcagctct ccactggctt    1980
ccttaccagc tcctctaacc acctgcattg agtctgtgag actagaatcc ctctctctgc    2040
ctccagtctg gtcgttgtga actctactga caactcattc agtgttttgc agccattctg    2100
tgagctaagt acatataata actgtgtgat gtacagtgtg tgatctgaga gtttatatta    2160
gtaactaaga ctgaagaaag agagcccagg ttggccagag acagttgtca atgttaatta    2220
ggactacttg gtaattatag ccagtgactt ggatggaact ggtaaattaa gacacatata    2280
tgaacacccg ttttcctggc atagctcact cattcagggt tttactcaca atattgtagc    2340
cttctagtga gtaaatagtc cattggcaaa gacattgcaa atactcaatt ttttttgcaa    2400
ataaatgaaa tatctggtga taggaagaaa attcaacatc cgtactatac cctggtcaac    2460
```

```
agagtctaag cttgttccgc caacccagtg cctggctcac agtacagtgt aacttcacac    2520
tgtgtagtgt gaaatctgac caaggtgtta ggaacagggg agccttccat cagcacctca    2580
tggggaatgg gtatacaaaa ataaataata aagcagaaaa gaagtgagga gacctcagat    2640
cacacatcta tgattattca tgtataagac gcgtatatac taccctacgg atttgtacct    2700
tacaaaagaa aactaagaga aatgttaatt gagggaggaa gatgagttat gtactaagga    2760
aaacgtgaat cctcaaatgg tgctgcctgt agggatccac agtacccaca gagtctgtgt    2820
taggaacagg tgacagtaac agtccttgac tagtttgtgt tgtcgtctag tttgtgttgt    2880
catgccagga actaccaggc atgtggcata agcatagaaa tgtcacattc agtgacccat    2940
aatgatataa acctttagt gaggaacaag gaacaaagag acagctcagt cccatactgc    3000
ttgcccgtca caagcatgag catttgagtt ccctccccag aacccacgca cactgtggtg    3060
gcacatgctt gtcatcccag tgcaggggac acacagagag aagtgcatct ctgggccttc    3120
ctcctcagcc tgcatagttg aattggtgac ttccagtata gactatctca aatacaatgt    3180
acttgacatt ctgaggagtg atatccaaag ataatgtgta gtctccatat gaacgagtat    3240
atgaacaagc tacggcatat atatatatat gtatgagtaa gttcccaaga dacaatattc    3300
ctgaggggga tatgggagct tttaatacga gttacaagat attatttatc cttctttctg    3360
gccattttta tgttcatatt tggctaagaa agaaacagct catatcttct tagttaataa    3420
ttttggaaga accattgttc aaacactggt gttgaggtgg aaggagatat attgagaaac    3480
gaagtcagac tccaagcatt agtctctgct attataagtc tcattttat aagagaatat    3540 tttcattgat gtttggtctg ttgctattgt attgtaacgt taaatctgta ctggaaggtc    3600
taagtctgtg agtgacttct cacatttata ctcttttgtt gtgcaaactt tgtaccttga    3660
tttataacta ttggttaaat aaaattggct acaacc                              3696

<210> SEQ ID NO 10
<211> LENGTH: 1490
<212> TYPE: DNA
<213> ORGANISM: Mus musculus

<400> SEQUENCE: 10
gccgcccgct gttttccctt gctgcagaca tgctgtggat ctgggctgtc ctgcctctgg      60
tgcttgctgg ctcacagtta agagttcata ctcaaggtac taatagcatc tccgagagtt     120
taaagctgag gaggcgggtt cgtgaaactg ataaaaactg ctcagaagga ttatatcaag     180
gaggcccatt ttgctgtcaa ccatgccaac ctggtaaaaa aaagttgag gactgcaaaa     240 tgaatggggg tacaccaacc tgcgccccat gcacagaagg gaaggagtac atggacaaga     300
accattatgc tgataaatgc agaagatgca cactctgcga tgaagagcat ggtttagagg     360
tggaaacaaa ctgcaccctg acccagaata ccaagtgcaa gtgcaaacca gacttctact     420
gcgattctcc tggctgtgaa cactgtgttc gctgcgcctc gtgtgaacat ggaaccttg      480 agccgtgcac agcaaccagc aatacaaact gcaggaaaca aagtcccaga aatcgcctat     540
ggttgttgac catccttgtt ttgttaattc cacttgtatt tatatatcga agtaccgga      600 aaagaaagtg ctggaaaagg agacaggatg accctgaatc tagaacctcc agtcgtgaaa     660
ccataccaat gaatgcctca aatcttagct tgagtaaata catcccgaga attgctgaag     720
acatgacaat ccaggaagct aaaaaatttg ctcgagaaaa taacatcaag gagggcaaga     780
tagatgagat catgcatgac agcatccaag acacagctga gcagaaagtc cagctgctcc     840
tgtgctggta ccaatctcat gggaagagtg atgcatatca agatttaatc aagggtctca     900
```

```
aaaaagccga atgtcgcaga accttagata aatttcagga catggtccag aaggaccttg      960
gaaaatcaac cccagacact ggaaatgaaa atgaaggaca atgtctggag tgaaaactac     1020
ctcagttcca gccatgaaga gaggagagag cctgccaccc atgatggaaa caaaatgaat     1080
gccaactgta ttgacattgg caactcctgg tgtgttctct ttgccagcaa atggtagttg     1140
atactcagtg agggtcaaat gactagcagg ttccagggac tgcttctgtt attctctgca     1200
gttgctgaga tgaaccattt tctctgtcta ctgcaatttt tacattcaaa tgtccatgaa     1260
atttgtatta aatgtgaagt ggaatctgca gtgtttgtgt ttatattcat atactatgaa     1320
ctgaggagaa ttataaactg aaacaaatac tcgcagttaa ttgaagacct tccattgatg     1380
gacagttctt ttcctctcta tgtggaaatg tataatagaa gaaataattt ttaaattaaa     1440
gtatctcttt ttgcatttcg aaaaaaaaaa aaaaaaaaa aaaaaaaaaa                 1490
```

POLYPEPTIDES COMPRISING FAS ACTIVATION AND NKG2D-LIGAND DOMAINS

CROSS REFERENCE TO RELATED APPLICATIONS

This application is a divisional of U.S. patent application Ser. No. 11/945,747, filed on Nov. 27, 2007, which claims the benefit of U.S. Provisional Patent Application Nos. 60/861,242, filed Nov. 28, 2006, and 60/907,586, filed Apr. 10, 2007. The contents of these applications are incorporated by reference in their entirety.

FIELD OF THE INVENTION

The present invention relates to compositions of polypeptides that comprise (a) a ligand for an NK stimulatory receptor and (b) a Fas activation domain; and to nucleic acids encoding such fusion proteins. The invention is also drawn to methods of constructing, and methods of using such compositions, including in the treatment or prevention of cancer.

BACKGROUND OF THE INVENTION

NK Stimulatory Ligands

Natural Killer (NK) cells are large granular bone marrow-derived lymphocytes that serve as an important component of innate immunity and can attack virally infected cells, transformed cells and tumor cells (Trinchieri, G. Biology of natural killer cells. *Adv. Immunol.* 47: 187-376 (1989), Diefenbach et al. Strategies for target cell recognition by natural killer cells. *Immunol. Rev.* 181: 170-184 (2001), Moretta et al. Activating receptors and coreceptors involved in human natural killer cell-mediated cytolysis. *Annu. Rev. Immunol.* 19: 197-223 (2001)). NK cells act as a "rapid force," responding faster than T cells and B cells as they do not have to rearrange the T cell receptor or the immunoglobulin genes to create a highly diverse repertoire of specificities against an antigen. Instead, NK cells recognize target cells by employing "missing-self" recognition [Ljunggren et al. In search of the 'missing self': MHC molecules and NK cell recognition. *Immunol. Today* 11: 237-244 (1990)].

NK cell activation is modulated by the balance between NK cell inhibitory receptor activity and NK stimulatory/activating receptor activity. Inhibitory NK receptor families include KIRs [Wilson et al. Plasticity in the organization and sequences of human KIR/ILT gene families. *Proc Natl Acad Sci USA* 97:4778 (2000)] in humans; the Ly-49 lectin-like homodimers [Takei et al. Ly49 and CD94/NKG2: developmentally regulated expression and evolution. *Immunol Rev* 181:90 (2001), Yokoyama et al. A family of murine NK cell receptors specific for target cell MHC class I molecules. *Semin Immunol* 7:89 (1995)] expressed in mice; and CD94-NKG2 lectin-like receptors expressed in both humans and mice. NK cell inhibitory receptors also bind to MHC class I molecules, which are important cell surface markers found in almost all cells, and are important in distinguishing self from non-self. The binding to these self-MHC molecules results in profound inhibition of the NK cell, and thus forms a basis for "missing self" recognition wherein the absence of MHC I leads to NK activation [Raulet et al. Regulation of the natural killer cell receptor repertoire. *Annu. Rev. Immunol.* 19: 291-330 (2001)].

A wide variety of NK cell activating receptors have been found in NK cells. See, e.g., Bahram et al., *Curr. Op. Immunol.* 2005, 17:505-519. Generally, activating receptors have short cytoplasmic domains and thus associate with transmembrane signaling adaptor molecules to activate NK cell function. NK cell activating receptors include NKG2A, NKG2C, NKG2D and NKG2E. Other activating receptors include: Natural Cytotoxicity Receptors (NCRs: NKp30, NKp44, NKp46); CD16 (responsible for ADCC); CD244 (2B4, can also make inhibitory signals); toll-like receptors (TLR); CD161; CD226 (DNAM-1); and CD96.

The sequence of NKG2A/C/E are highly related to each other and to C-type lectins. NKG2A/C/E are type-2 transmembrane receptors that are present in the NK cell membrane as heterodimers with another protein (CD94) and bind to non-classical MHC class 1 molecules known as HLA-E (in humans) or Qa1 (in mice) (Braud et al. Functions of nonclassical MHC and non-MHC-encoded class I molecules. *Curr. Opin. Immunol.* 11: 100-108 (1999)).

NKG2D, in contrast, is a homodimeric C-type lectin-like protein that is expressed by all NK cells, subsets of NKT cells and subsets of gamma delta T cells [Bauer et al. Activation of NK cells and T cells by NKG2D, a receptor for stress-inducible MICA. *Science* 285, 727-729 (1999), Diefenbach et al. Ligands for the murine NKG2D receptor: expression by tumor cells and activation of NK cells and macrophages. *Nat. Immunol.* 1: 119-126 (2000), Jamieson et al. The role of the NKG2D immunoreceptor in immune cell activation and natural killing. *Immunity* 17: 19-29 (2002)]. After stimulation, NKG2D is also expressed by virtually all CD8+ T cells and macrophages in mice [Diefenbach et al. Ligands for the murine NKG2D receptor: expression by tumor cells and activation of NK cells and macrophages. *Nat. Immunol.* 1: 119-126 (2000), Jamieson et al. The role of the NKG2D immunoreceptor in immune cell activation and natural killing. *Immunity* 17: 19-29 (2002)].

Several distinct ligands for NKG2D have been identified, most of which are poorly expressed in normal cells but can be upregulated in infected, transformed and/or stressed cells. NKG2D ligands in humans include MHC class 1-chain-related protein A (MICA) and MICB (Bauer—1999), UL-16-binding proteins (ULBP) [Cosman et al. ULBPs, novel MHC class I-related molecules, bind to CMV glycoprotein UL16 and stimulate NK cytotoxicity through the NKG2D receptor. *Immunity* 14: 123-133 (2001)] and RAET1 [Radosavljevic et al. A cluster of ten novel MHC class I related genes on human chromosome 6q24.2-q25.3. *Genomics* 79: 114-123 (2002)]. The ULBP and RAET1 families are encoded on the syntenic region on human chromosome 6.

Mouse NKG2D ligands include histocompatibility 60 (H60) (Malarkannan et al. The molecular and functional characterization of a dominant minor H antigen, H60. *J. Immunol.* 161: 3501-3509 (1998)), Mouse UL16-binding protein-like transcript 1 (Mult1) (Carayannopoulos et al. Cutting edge: murine UL16-binding protein-like transcript 1: a newly described transcript encoding a high-affinity ligand for murine NKG2D. *J. Immunol.* 169: 4079-4083 (2002), Diefenbach et al. A novel ligand for the NKG2D receptor activates NK cells and macrophages and induces tumor immunity. *Eur. J. Immunol.* 33: 381-391 (2003)) and the retinoic acid early transcript 1 (Rae1) and its five alleles with >98% amino acid identity known as Rae1α-Rae1ε (Nomura et al. Genomic structures and characterization of Rae1 family members encoding GPI-anchored cell surface proteins and expressed predominantly in embryonic mouse brain. *J. Biochem.* 120: 987-995 (1996), Zou et al. Isolation and characterization of retinoic acid-inducible cDNA clones in F9 cells: a novel cDNA family encodes cell surface proteins sharing partial homology with MHC class I molecules. *J. Biochem.* 119: 319-328 (1996)). The Rae1, H60 and Mult1 families are only 20-28% homologous with each other. Interestingly, and analogous to human ULBP and RAET1, all known ligands for mouse NKG2D map close to the telomeric region of mouse chromosome 10 [Diefenbach et al. Ligands for the murine NKG2D receptor: expression by tumor cells and activation of NK cells and macrophages. *Nat. Immunol.* 1: 119-126 (2000); Malarkannan et al. The molecular and functional characterization of a dominant minor H antigen, H60. *J. Immunol.* 161: 3501-3509 (1998); Nomura et al. Genomic structures and characterization of Rae1 family members encoding GPI-anchored cell surface proteins and expressed predominantly in embryonic mouse brain. *J. Biochem.* 120: 987-995 (1996)].

Tumor cells have developed many strategies for escaping immune surveillance, one of the ways is to shed the NKG2DL such as MICA (Groh et al. Tumor-derived soluble MIC ligands impair expression of NKG2D and T-cell activation. Nature 419:734-8 (2002); Salih et al. Cutting edge: downregulation of MICA on human tumors by proteolytic shedding. *J Immunol* 2002; 169:4098-102) or ULBP2. Shedding of these ligands reduces the NKG2DL surface levels and effect the susceptibility to cytolysis by NK cells.

FAS

Higher organisms have developed several mechanisms to ensure the rapid and selective elimination of unwanted cells in various biological processes such as development, maintenance of tissue homeostasis, and elimination of cancer cells. One method of programmed cell death involves the interaction of cell surface Fas/CD95 with its cognate ligand, FasL/CD95L (Houston et al. The Fas signaling pathway and its role in the pathogenesis of cancer. *Curr Opin Pharmacol.* 4(4):321-6 (2004)).

Structurally, Fas is a transmembrane cell surface receptor containing three cysteine-rich extracellular domains at the amino terminus, which are responsible for ligand binding, and an intracytoplasmic death domain (DD) of about 80 amino acids that is essential for transducing the apoptotic signal [Peter et al. The CD95 (APO-1/Fas) DISC and beyond. *Cell Death Differ* 10:26-35 (2003)]. Binding of FasL to Fas causes a higher-order aggregation of the receptor molecules and recruitment of the adaptor molecule Fas-associated death domain (FADD) via DD-DD interactions. FADD also has another domain called the death effector domain, which in turn recruits pro-caspase-8 (FLICE) and/or pro-caspase-10 to the receptor. The resulting multimeric protein complex is called the death-inducing signaling complex (DISC), and forms within seconds of receptor engagement [Peter-2003].

Tumor cells may use the Fas signaling pathway to evade the immune response. One common mechanism is to decrease sensitivity of tumor cell to Fas-mediated apoptosis by regulating cell surface expression of Fas [Moller et al. Expression of APO-1 (CD95), a member of the NGF/TNF receptor superfamily, in normal and neoplastic colon epithelium. *Int J Cancer* 57:371-377 (1994); Ivanov et al. FAP-1 association with Fas (Apo-1) inhibits Fas expression on the cell surface. *Mol Cell Biol* 23:3623-3635 (2003)]. In this approach tumors cells escape killing by NK cells and other effector cells by failing to express FAS receptor. Alternate approaches for evading the immune response include the secretion of an antagonistic 'decoy' receptor [Pitti et al. Genomic amplification of a decoy receptor for Fas ligand in lung and colon cancer. Nature 396:699-703 (1998)]; expression of anti-apoptotic molecules such as BCL2 family members (Sarid et al. Kaposi's sarcoma-associated herpesvirus encodes a functional bcl-2 homologue. *Nature Med.* 3: 293-298 (1997); Boise et al. BCL-X, a BCL-2-related gene that functions as a dominant regulator of apoptotic cell death. *Cell* 74: 597-608 (1993)); down regulation and mutation of pro-apoptotic genes like BAX, APAF1 and CD95 (Ionov et al. Mutational inactivation of the proapoptotic gene BAX confers selective advantage during tumor clonal evolution. *Proc. Natl. Acad. Sci. USA* 97: 10872-10877 (2000); Soengas et al. Inactivation of the apoptosis effector Apaf-1 in malignant melanoma. *Nature* 409: 207-211 (2001); Teitz et al. Caspase-8 is deleted or silenced preferentially in childhood neuroblastomas with amplification of MYCN. *Nature Med.* 6: 529-535 (2000); Strand et al. Lymphocyte apoptosis induced by CD95 (APO-1/Fas) ligand-expressing tumor cells—a mechanism of immune evasion? *Nature Med.* 2: 1361-1366 (1996)); alterations of p53 pathway (Bunz et al. Disruption of p53 in human cancer cells alters the responses to therapeutic agents. *J. Clin. Invest.* 104: 263-269 (1999); Schmitt et al. INK4A/ARF mutations accelerate lymphomagenesis and promote chemoresistance by disabling p53. *Genes Dev.* 13: 2670-2677 (1999)) or alterations of p13KT/AKT pathway (Kauffmann-Zeh et al. Suppression of c-Myc-induced apoptosis by Ras signaling through PI(3)K and PKB. *Nature* 385: 544-548 (1997); Chang et al. Transformation of chicken cells by the gene encoding the catalytic subunit of PI 3-kinase. *Science* 276: 1848-1850 (1997)). Cancer cells may also express FasL to induce apoptosis in immune cells.

The present specification describes a new and novel way of combating cancer by combining NK stimulatory molecules (such as Mult1) and a death domain (such as found in Fas). The engagement of NK cells and/or other immune cells with tumor cells expressing the fusion protein not only sends an apoptotic signal to the tumor cells but also activates the NK cells through the NKG2D receptor so that not only the engaged tumor cells will be killed via Fas induced-mechanisms but also are lysed directly by the activated NK cells.

BRIEF SUMMARY OF THE INVENTION

The present invention relates to novel polypeptides, polynucleotides encoding them and methods related thereto.

In one embodiment, the invention is drawn to a polypeptide comprising (i) a ligand for a stimulatory Natural Killer (NK) receptor and (ii) an intracytoplasmic death domain (DD). Such polypeptides may be fusion proteins, for example, comprising suitable ligand domains and DD domains from proteins available in the art.

Suitable ligands for stimulatory NK cell receptors include ligands for NKG2D, such as MHC class 1-chain-related protein A (MICA); MICB; UL-16-binding proteins (ULBP); RAET1; histocompatibility 60 (H60); Mouse UL16-binding protein-like transcript 1 (Mult1); the retinoic acid early transcript 1 (Rae1) and its five alleles Rae1α-Rae1ε; and fragments thereof. Suitable ligands may bind the long form of the NKG2D, the short form of NKG2D, or both forms. Suitable ligands may bind other activating receptors including Ly49D (ligand: H-2D$^d$), and Ly49H (ligand: m157), but not inhibitory receptors such as NKG2A, or Ly49C/I/A/G2. Suitable ligands also include functional homologues that may be generated by those of ordinary skill in the art.

In some embodiments, the NKG2D ligand is Mult1 (SEQ ID NO:1), or a fragment thereof, including amino acids 1-211 of SEQ ID NO:1. Also included are functional homologues of Mult1 (i.e. NKG2D receptor binding), including polypeptides with an amino acid sequence 70%, 75%, 80%, 85%, 90%, 95%, 97% or 99% identical to amino acids 1-211 of SEQ ID NO:1. Amino acid additions, deletions and substitutions are also included. Suitable Mult1 variants include those having any one, some, or all, of the NKG2D binding sites. A cDNA sequence encoding Mult 1 is presented as SEQ ID NO: 9.

A suitable intracellular death domain (DD) includes the intracellular death domain of Fas (SEQ ID NO:2), especially amino acids 166-327 of SEQ ID NO:2. The death domain may also be obtained from the tumor necrotic factor receptor-1 (TNFR1) and the TRAIL (TNF-related apoptosis inducing ligand) receptors DR4 and DR5. A cDNA sequence encoding Fas is presented as SEQ ID NO: 10.

Also suitable are functional homologues of such DD-containing proteins, including those that with amino acid additions, deletions and substitutions relative to the parent protein. In some embodiments, the invention includes polypeptides with an amino acid sequence that is 70%, 75%, 80%, 85%, 90%, 95%, 97% or 99% identical to amino acids 166-327 of SEQ ID NO:2.

In some embodiments therefore, the invention is drawn to a polypeptide comprising a fusion of at least the extracellular domain of Mult1 and the intracellular death domain of Fas, and having the amino acid sequence of SEQ ID NO:3. In related embodiments, the polypeptide has a sequence that is 70%, 75%, 80%, 85%, 90%, 95%, 97% or 99% identical to SEQ ID NO:3. Amino acid additions, deletions and substitutions are also included.

In further embodiments, the invention comprises polynucleotides which encode a polypeptide comprising (i) a ligand for a stimulatory Natural Killer (NK) receptor and (ii) an intracytoplasmic death domain (DD). Suitable stimulatory NK receptors and DD are described elsewhere herein. In some embodiments, the polynucleotide encodes a fusion between a NKG2D ligand such as Mult1 and the Fas DD. In an additional embodiment comprises a fusion between the extracellular region of Mult1 and the transmembrane and intracellular regions of Fas. In a related embodiment, the polynucleotide comprises 7-1,134 of SEQ ID NO:4. In other embodiments, the polynucleotide is 70%, 75%, 80%, 85%, 90%, 95%, 97% or 99% identical 7-1,134 of SEQ ID NO:4.

In related embodiments, a polynucleotide with the sequence of 7-1134 in SEQ ID NO:4 is operatively linked to a promoter. Suitable promoters may be constitutive, or may be upregulated in cancer cells.

In further embodiments, the invention is a composition comprising any of the polynucleotides and/or polypeptides described herein, and a pharmaceutically acceptable excipient.

The polynucleotides, polypeptides and compositions are useful in the practice of various methods, including therapeutic methods. The invention therefore includes a method of promoting NK-mediated killing of a target cell by delivering a polynucleotide to said target cell. Such a method may be utilized in the treatment of cancer by delivering the fusion peptide to a target cell, including by direct injection into a tumor. Such polypeptides can be delivered by administered the polypeptide to a patient, or by administration of a polynucleotide encoding such a polypeptide to a patient. Delivery of a polynucleotide may occur with naked DNA but may also facilitated, such as by the use of cationic lipids, particle bombardment or by packaging polynucleotides in a virus. Suitable viruses include, for example, Adenovirus, Adeno-Associated virus, Retrovirus, and Poliovirus, and may be chosen depending on the targets. In some embodiments, the virus is an adenovirus, and particularly the Onyx-15 adenovirus, which has been demonstrated to be useful in treating cancer. The viral vectors can be delivered directly into tumors by injection; they can also be delivered systematically, especially if the vectors are tumor specific.

Accordingly, the present invention provides novel and highly effective treatments for cancer. One of ordinary skill in the art may further modify the methods described herein to optimize a treatment protocol for a given cancer. Suitable modifications include choice of death domain and ligand for a stimulatory NK receptor; promoter; dose, route and means of administration; and the use of additional therapies including surgery, radiation, chemotherapy, vaccination, and immune stimulation. Such embodiments are further included within the scope of the present invention.

BRIEF DESCRIPTION OF THE DRAWINGS

FIG. 2A, $5\times10^5$ cells of TC-1 and clones L5, L7, or L10 were stained with purified rat anti-mouse MULT1 antibody followed by goat anti-rat IgG F(ab)-FITC. (dark lines). Dashed/light lines are controls, in which the MULT1 antibody was replaced with nonspecific antibody of the same isotype. The cells were analyzed on FACS Calibur with CellQuest software. High levels of fusion protein, Mult1/Fas were expressed on the cells of clones L-5 and L-10, but not on cells of TC-1 or clone L-7.

FIG. 2B. $1\times10^6$ cells of TC-1 or clones L5, L7, or L10 were first treated with NKG2D/Fc and then stained with anti-mouse NKG2D antibody conjugated with FITC. Results are shown with dark lines compared with dashed/light lines as the isotype control.

FIG. 2C. In vitro tumor growth. $1\times10^5$ tumor cells of TC-1, L-5, L-7 or L-10 were inoculated in culture wells and cultured. The numbers of cells in each well were counted after 3 and 6 days of culture. At day 3, there were no significant difference among these clones. At day 6, the number of TC-1 tumor cells were significantly higher than that of the other clones. However, there was no significant difference among clones L-5, L-7, and L-10.

FIG. 2D RT-PCR. Lanes 1, 3, 5, 7: RT-PCR products from RNAs of TC-1 cells and clones of L-5, L-7, and L-10 using MULT1 primers, which product is 646 bp; Lanes 2, 4, 6, 8: RT-PCT products from RNAs of TC-1 cells and clones of L-5, L-7, and L-10 using primers for β-actin as controls; line 9:1 kb marker.

FIG. 2E. RT-PCR. Lanes 1-4: RT-PCT products from RNAs of TC-1 cells and clones of L-5, L-7, and L-10 using primers primers covering the entire fusion gene sequences, which product is 1134 bp; Lanes 5-8: RT-PCT products from RNAs of TC-1 cells and clones of L-5, L-7, and L-10 using primers for β-actin as controls; Lane 9:1 kb marker.

FIGS. 3A-D MULT1E/FasTI induces apoptosis. $1\times10^6$ cells of TC-1 and clones L-5, L-7, and L-10 were treated with 1 µg/ml NKG2D/Fc for 16 hours. The cells were then analyzed for apoptosis and necrosis using Annexin-V assay (FIGS. 3A, B, and C) or Caspase 3 assay (FIG. 3D) according to the manufacturers' protocols. FIG. 3A represents an example of the FACS data. FIGS. 3B and 3C are summaries of data from three separate experiments. The statistical analyses were conducted between the controls (open bars) and NKG2D/Fc treated cells (solid bars) using Two-way ANOVA. The difference between NKG2D/Fc treated L-5 cells and NKG2D/Fc treated L-10 cells was also compared using student t test. *: p<0.05; : p<0.01; *: p<0.001.

FIG. 4A-B. MULT1E/FasTI activates NK cells. $1 \times 10^6$ cells of TC-1 and clones L-5, L-7, and L-10 were cocultured with NK cells for three hours. The cells were stained with anti-NK1.1-FITC. The cells were then permeablized and fixed, and stained with anti-mouse IFN-γ-PE. The cells were analyzed on FACS Calibur with CellQuest software. FIG. 4A represents an example of the FACS data. FIG. 4B is the summary of data from three separate experiments. *: p<0.05.

Figure 5:
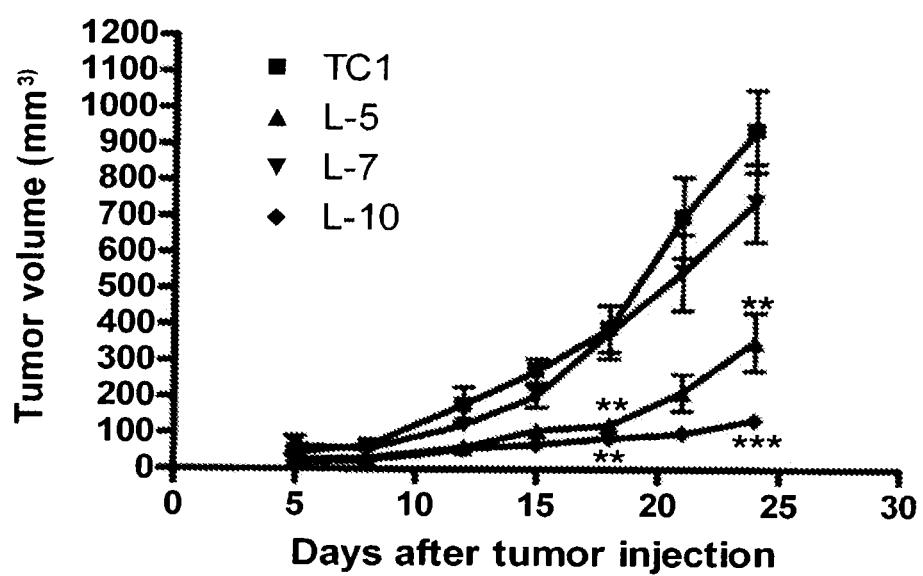

FIG. 5. Subcutaneous tumor study. $2 \times 10^5$ tumor cells of TC-1 or clones L-5, L-7, and L-10 in 0.2 ml PBS were s.c. injected into C57BL/6J mice (4 mice/group). Tumor growth was measured and presented as $1/2 LW^2$. *: p<0.05; ***: p<0.001.

Figure 6:
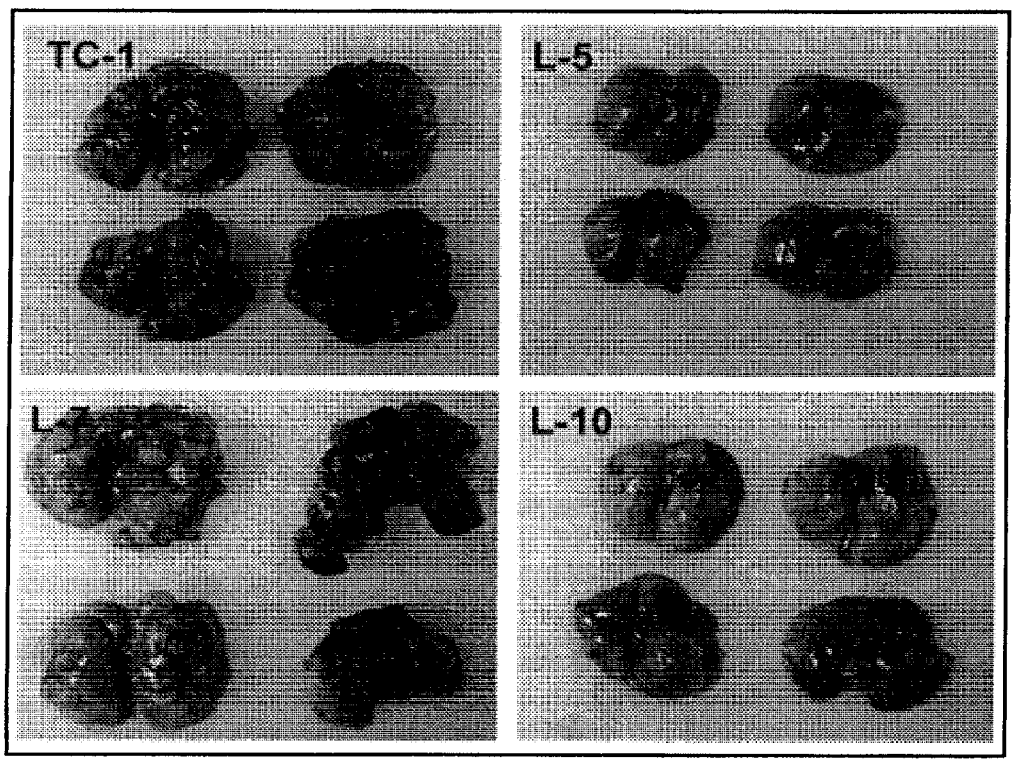

FIG. 6A-C. Pulmonary metastasis. $2 \times 10^5$ tumor cells of clones TC-1, L-5, L7, or L-10 were i.v. injected into C57BL/6J mice. Four weeks later, mice were sacrificed and lungs were isolated and weighed. The number of tumor nodules on the lungs were counted. FIG. 6A, Photos of the lungs; FIG. 6B, Weight of the lungs; 6C, Numbers of tumor nodules on the lungs.

DETAILED DESCRIPTION OF THE INVENTION

Terms

For the purposes of the present application, the following terms have these definitions:

As used herein "a" or "an" means one or more, unless specifically indicated to mean only one.

"About" generally means the stated value plus or minus a range of 10% of that value.

"Administration" as used herein encompasses all suitable means of providing a substance to a patient. Common routes include oral, sublingual, transmucosal, transdermal, rectal, vaginal, subcutaneous, intramuscular, intravenous, intra-arterial, intrathecal, via catheter, via implant etc. In some embodiments, a composition is administered near or directly to the tumor, such as by direct injection into the tumor or injection into the blood such as when the tumor is a tumor of the blood.

"Cancer" as used herein is not limited to any particular type of cancer. Carcinomas may include adenocarcinoma, which develop in an organ or gland, and squamous cell carcinoma, which originate in the squamous epithelium. Other cancers that can be treated include sarcomas, such as osteosarcoma or osteogenic sarcoma (bone), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), an esenchymous or mixed mesodermal tumor (mixed connective tissue types). In addition myelomas, leukemias, and lymphomas are also susceptible to treatment.

"DD" as used herein refers to an intracytoplasmic death domain. Such death domains (DDs) may be those that are found in Fas, and which mediate Fas-dependent apoptosis. However, a DD includes those from other proteins which cause cell death, whether via apoptosis or through other mechanisms.

"NK cell" as used herein refers to a natural killer cell, such as found in man and other animals. The term is not intended to be restricted to NK cells of any given species.

"Patient" as used herein includes any vertebrate animal, including equine, ovine, caprine, bovine, porcine, avian, canine, feline and primate species. In one embodiment, the patient is human. A person of ordinary skill in the art will recognize that particular immune co-stimulatory molecules, signaling molecules, cell markers, cell types, infectious agents etc., discussed with reference to one species, may have corresponding analogues in different species, and that such analogues, and their use in corresponding and related species, are encompassed by the present invention.

"Tumor" as used herein includes solid and non solid tumors (such as leukemia), and different stages of tumor development from pre-cancerous lesions and benign tumors, to cancerous, malignant and metastatic tumors. Representative tumor cells against which this invention is useful include, without limitation, carcinomas, which may be derived from any of various body organs including lung, liver, breast, bladder, stomach, colon, pancreas, skin, and the like.

Overview

Tumor cells are characterized by misregulated or unregulated growth, as they are not sensitive to the normal inhibitory signals that limit cell division. Fortunately, many tumor cells may be targeted and killed by the immune system. However, tumor cells have developed many strategies for escaping immune surveillance and destruction. Tumor cells that are able to escape immune surveillance and destruction can continue to grow and ultimately cause cancer in the patient. However, the present invention seeks to use such differences in cancer cells as a means to specifically target their destruction.

NK Stimulatory Ligands

As described elsewhere herein, NK cells are important in the target killing of cancer cells, often using "missing self" recognition. As MHC molecules are inhibitory to NK cells, NK cells are not normally activated by normal cells. Thus, a cancer cell that down regulates MHC receptors to avoid recognition and attack by T-cells and macrophages, will be recognized as "non-self" by the NK cells and targeted for destruction. To avoid NK-cell mediated killing, a cell may therefore down regulate expression of NK-stimulatory ligands. One means is to shed the NKG2DL such as MICA (Groh et al. *Nature* 419:734-8 (2002); Salih et al. *J. Immunol* 169:4098-102 (2002)) or ULBP2. Shedding of these ligands reduces the NKG2DL surface levels and effect the susceptibility of to NKG2D cytolysis by NK cells.

The present invention seeks to overcome this problem by providing NK-stimulatory ligands to target cells in order to promote NK killing of such target cells. This may be done by directly providing the protein or, preferably, by administration of a nucleic acid to a cell such that ultimately it expresses the protein on its surface.

Suitable NK-stimulatory ligands for use in the invention include Mult1, Rae1, H60, MICA/B, RAET1-3, ULPB4, H-$2D^d$, and m157, Suitable ligands also include functional homologues that may be generated by those of ordinary skill in the art. In a some embodiments, the ligand is an NKG2D ligand. A preferred embodiment is Mult1.

The amino acid sequence of Mult1 is set forth in SEQ ID NO:1. Amino acids 1-211 encode the extracellular portion of Mult1. Particularly useful in the present invention are domains which bind to NKG2D.

Advantageously, if the cell is escaping immune surveillance by repression of NK-stimulatory ligands, or production of mutant variants, transformation of a cell with a polynucleotide encoding the stimulatory ligand will overcome such tactics. Particularly useful is the ability to put expression of the stimulatory ligand under the control of a promoter different to that normally regulating the ligand in a host, and expressing the ligand at higher levels and/or in response to signals found in cancer cells.

Intracytoplasmic Death Domains (DD)

Higher organisms have developed several mechanisms to ensure the rapid and selective elimination of unwanted cells in various biological processes such as development, maintenance of tissue homeostasis and elimination of cancer cells. The most well studied method of programmed cell death involves the interaction of cell surface Fas/CD95 with its cognate ligand, FasL/CD95L. Houston et al. "The Fas signalling pathway and its role in the pathogenesis of Cancer," Curr Opin Pharmacol. 4(4):321-326 (2004). Tumor cells may use the Fas signaling pathway to evade the immune response. One common mechanism is to decrease sensitivity of tumor cell to Fas-mediated apoptosis by regulating cell surface expression of Fas. Moller et al. "Expression of APO-1 (CD95), a member of the NGF/TNF receptor superfamily, in normal and neoplastic colon epithelium" Int J Cancer 57:371-377 (1994); Ivanov et al. "FAP-1 association with Fas (Apo-1) inhibits Fas expression on the cell surface," Mol Cell Biol 23:3623-3635 (2003). In this approach tumors cells escape killing by NK cells and other effector cells by failing to express FAS receptor.

Other alternate approaches are secreting an antagonistic 'decoy' receptor (Pitti et al. "Genomic amplification of a decoy receptor for Fas ligand in lung and colon cancer," Nature 396:699-703 (1998)); expression of anti-apoptotic molecules such as BCL2 family members (Sand et al. "Kaposi's sarcoma-associated herpesvirus encodes a functional bcl-2 homologue," Nature Med. 3, 293-298 (1997); Boise et al. "BCL-X, a BCL-2-related gene that functions as a dominant regulator of apoptotic cell death," Cell 74: 597-608 (1993)); down regulation and mutation of pro-apoptotic genes like BAX, APAF1, CD95 (Ionov et al. "Mutational inactivation of the proapoptotic gene BAX confers selective advantage during tumor clonal evolution," Proc. Natl. Acad. Sci. USA 97: 10872-10877 (2000); Soengas et al. "Inactivation of the apoptosis effector Apaf-1 in malignant melanoma," Nature 409: 207-211 (2001); Teitz et al. "Caspase-8 is deleted or silenced preferentially in childhood neuroblastomas with amplification of MYCN," Nature Med. 6: 529-535 (2000); Strand et al. "Lymphocyte apoptosis induced by CD95 (APO-1/Fas) ligand-expressing tumor cells—a mechanism of immune evasion?" Nature Med. 2: 1361-1366 (1996)); alterations of p53 pathway (Bunz et al. "Disruption of p53 in human cancer cells alters the responses to therapeutic agents," J. Clin. Invest. 104: 263-269 (1999); Schmitt et al. "INK4A/ARF mutations accelerate lymphomagenesis and promote chemoresistance by disabling p53," Genes Dev. 13: 2670-2677 (1999)); alterations of p13KT/AKT pathway (Kauffmann-Zeh et al. "Suppression of c-Myc-induced apoptosis by Ras signalling through PI(3)K and PKB," Nature 385: 544-548 (1997); Chang et al. "Transformation of chicken cells by the gene encoding the catalytic subunit of PI 3-kinase," Science 276: 1848-1850 (1997); or expression of FasL by cancer cells in order to induce apoptosis in immune cells targeting the cancer.

Accordingly, in the present invention, administration of a Fas death domain (either by direct administration of a polypeptide or administration of a polynucleotide encoding the Fas death domain) will provide a means for Fas-mediated killing of cancer cells. If provided by means of a polynucleotide, Fas DD expression may be controlled by a promoter immune to suppression by the cancer cell, delivering high levels of Fas DD. Expression may also be controlled such that the DD is maximally expressed in cancer cells.

The sequence of Fas is set forth in SEQ ID NO:2. Amino acids 166-327 comprise the intracellular domain, which contains the intracytoplasmic death domain.

The present invention is not limited to Fas DD however, but also includes other domains that induce cell death. Preferably, cell death is induced by apoptosis. Some cancer cells can resist Fas-mediated killing by manipulation of the apoptosis pathway downstream of Fas. Therefore, the use of DD from other pathways may be used to kill such "Fas-resistant" cancers. These include, for example, the tumor necrotic factor receptor-1 (TNFR1) and the TRAIL (TNF-related apoptosis inducing ligand) receptors DR4 and DR5.

Fusion Proteins

The present invention is directed to fusion proteins, polynucleotides which encode them, methods of making them and their use, particularly in cancer therapeutics. Typically, the fusion protein possesses (a) a ligand for a stimulatory NK-cell receptor (b) an intracytoplasmic death domain and (c) a means of linking the intracellular and extracellular domains of the protein. Preferably, the ligand for a stimulatory NK cell receptor is the extracellular portion of the fusion protein, and the intracytoplasmic DD is the intracellular portion of the fusion protein.

The extracellular and intracellular domains of the present invention are linked via linking means. Preferably, such a linking means comprises at least a transmembrane domain. Such a transmembrane domain may be derived from, for example, the transmembrane domains of the ligand for the stimulatory NK-cell receptor, the intracytoplasmic DD, both, or any source, provided that such a domain possesses suitable properties for anchoring within the lipid bilayer.

In one embodiment, the fusion protein is constructed from extracellular domain of Mult1, the intracellular domain of Fas, and a transmembrane domain from Fas. The amino acid sequence of the Mult1/Fas fusion is recited as SEQ ID NO:3. The DNA sequence encoding this fusion protein is provided in SEQ ID NO:4.

While not wishing to be bound by any theory on the fusion protein, it is proposed that the fusion protein works in the following manner. When the fusion protein is expressed on a tumor cell, the presence of an NK-stimulatory ligand activates the NK cell, thereby triggering the release of cell killing factors. At the same time, the binding interaction between the NK stimulatory ligand and the NK receptors transduce a signal to the intracellular death domain in the target cell. Thus, interaction between the NK receptor and the fusion protein triggers target cell death by two independent mechanisms: one from NK-cells, the other from the DD.

The expression of NKG2D stimulatory ligands and the induction of cell killing may also induce other elements of the immune system to respond to a cancer. The activation of the adaptive arm of the immune system makes it more likely that the body will develop active immunity against tumor associated antigens and thereby provide long term immunity to the cancer.

Thus, in one exemplary embodiment, an extracellular MULT1 domain activates NK cells; and the intracellular region of FAS transmits an apoptotic signal. In another embodiment, the Mult1 extracellular domain is fused to the transmembrane and intracellular domains of Fas, creating a Mult1/Fas fusion protein designated MultE/FasTI. Thus, the MULT1/FAS fusion proteins, when expressed on a tumor cell, activate an NK cell through the MULT1-NKG2D receptor interaction and at the same time transmit intracellular apoptotic signal through FAS, which ultimately results in death of the fusion protein-expressing cells by any of two independent pathways.

Because the fusion protein provides stimulates two independent pathways leading to cell death it bifunctional and is more effective at killing a cancer cell than the use of one pathway alone. That is, for a MULT1/Fas fusion protein, death is caused both by Fas-mediated apoptosis and NK-mediated apoptosis. Both killing pathways are activated simultaneously.

Also, the two pathway approach makes the fusion protein applicable to a broader range of cancers. Cancers develop ways to avoid immune surveillance, such as alteration of the Fas pathway, or down regulation the expression of NK-stimulatory ligands. It is significantly less likely that the cancer will have simultaneously mutated both pathways. Further, the use of a bifunctional molecule will also decrease the chance that a cancer will develop resistance to both pathways.

The development of adaptive immunity may be further enhanced by the use of a non-self antigen, such as Mult1 in humans, thereby provoking a specific T cell and antibody response against non-self elements. If the expression of non-self antigens is limited to cancer cells (such as, by direct injection of DNA into a tumor, and/or ensuring that expression is cancer specific) then a potent additional means of clearing the body of cancer may be developed.

In addition, the present invention provides more effective and novel means of killing cancer cells, and can provide a better "therapeutic window:" in other words, the amount of composition required to effect anti-cancer therapy is significantly below the amount that causes side effects. Many cancer therapies suffer from a narrow therapeutic window. In fact, most of the protein cancer drugs delivered through gene therapy are only effective in the cells that express them. In contrast, the current invention can not only kill tumor cells that express the fusion protein through apoptosis and NK cell killing, but also the surrounding tumor cells that do not express the fusion protein via NK cell killing. Considering the fact the most efficient gene delivery methods is not a hundred percent, the current invention bears a huge advantage.

Homologues

The DD and stimulatory NK receptor ligand of the present invention also includes conservative variants of the DD and stimulatory NK receptor ligand. The overall structure and composition of the two, in that respect, are important only insofar as they confer the appropriate functional characteristics, i.e., stimulatory NK receptor ligand, and transmission of a cell death signal, such as via apoptosis induction.

Conservative variants according to the invention generally conserve the overall molecular structure of the protein domains. Given the properties of the individual amino acids comprising the disclosed protein products, some rational substitutions will be apparent. Amino acid substitutions, i.e. "conservative substitutions," may be made, for instance, on the basis of similarity in polarity, charge, solubility, hydrophobicity, hydrophilicity, and/or the amphipathic nature of the residues involved.

For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

Conservative variants specifically contemplate truncations of the presently described receptor antagonizing domains. Truncations may be made from the N- or C-terminus, but generally do not entail deleting more than about 30% of the native molecule. More preferably, less than about 20%, and most preferably, less than about 10%, of the native molecule is deleted.

In general, both the DNA and protein molecules of the invention can be defined with reference to "sequence identity." Some molecules have at least about 50%, 55% or 60%, 65%, 65%, 70%, 80%, 85%, 90%, 95%. As used herein, two nucleic acid molecules or proteins are said to "share significant sequence identity" if the two contain regions which possess greater than 85% sequence (amino acid or nucleic acid) identity.

"Sequence identity" is defined herein with reference the Blast 2 algorithm, which is available at the NCBI (http://www.ncbi.nlm.nih.gov/BLAST), using default parameters. References pertaining to this algorithm include: those found at http://www.ncbi.nlm.nih.gov/BLAST/blast_references.html; Altschul, et al. "Basic local alignment search tool." *J. Mol. Biol.* 215: 403-410 (1990); Gish, W. & States, D. J. "Identification of protein coding regions by database similarity search." *Nature Genet.* 3: 266-272 (1993); Madden et al. "Applications of network BLAST server" *Meth. Enzymol.* 266: 131-141 (1996); Altschul et al. "Gapped BLAST and PSI-BLAST: a new generation of protein database search programs." Nucleic Acids Res. 25: 3389-3402 (1997); and Zhang, J. & Madden, T. L. "PowerBLAST: A new network BLAST application for interactive or automated sequence analysis and annotation." *Genome Res.* 7: 649-656 (1997). Accordingly, the peptide sequences from different species can be aligned, using standard computer programs like BLAST, to inform further variation domains that preserve their essential function.

Polynucleotides

The present invention includes polynucleotides and methods of using such polynucleotides. In one embodiment the polynucleotide has the sequence of SEQ ID NO:4 especially nucleotides 7-1134 of SEQ ID NO:4, encoding a fusion protein. The invention also includes homologues, as described elsewhere herein.

Nucleic acids administered to an animal are taken up by the cell. If the nucleic acid is DNA, it is typically necessary for the DNA to enter the nucleus where it is transcribed. Nuclear localization may be enhanced by the addition of nuclear localization signals (such as peptides tagged onto the DNA), or by packaging in a virus.

mRNA does not require nuclear localization, but generally has a much shorter half life than DNA. The half life of mRNA may be manipulated by means known to those of ordinary skill in the art.

Means of delivering polynucleotides to a cell, either in vitro or in vivo, are well known in the art. See, e.g., "Vector Targeting for Therapeutic Gene Delivery," by David T. Curiel and Joanne T. Douglas. 2002 Culinary and Hospitality Industry Publications Services. "Naked" DNA (i.e. free from transfection facilitating agents), can be used to deliver therapeutic proteins and antigens. Delivery can be enhanced by addition of transfection facilitating agents, such as ions, cationic lipids, liposomes, transforming proteins, or packaging inside a viral particle such as a retrovirus or adenovirus.

Delivery of a polynucleotide encoding a fusion proteins of the present invention has a number of advantages over the use of proteins per se. First, expression in the cell and subsequent processing and trafficking can ensure that the fusion protein is correctly situated in the cell membrane, with the NK stimulatory ligand extracellular and the DD domain intracellular. Second, a transfected cell can express a protein for a long period of time and at high levels, ensuring that the fusion protein is expressed for sufficient time and at sufficient levels to result in killing of the cancer cell.

Third, the level of expression may be manipulated by the selective use of different promoters. One may choose a promoter that is constitutive or regulated, and is expressed at high or low levels, as desired. Particularly useful is the ability to tailor expression for a given cancer. For example, a promoter for a gene that is upregulated in cancer.

Fourth, nucleic acids, especially DNA, are stable and so can be stored for long periods of time. A therapeutic composition may last longer if stored as DNA rather than as the protein product encoded by the DNA. Thus, there is less wastage, greater economic efficacy, and even the ability to deliver therapeutic compositions without an expensive cold chain.

Viral Delivery Systems

In some embodiments, the polynucleotides of the invention may be delivered using a viral vector. Any viral vector (including those with DNA or RNA genomes) are suitable as vectors. Commonly used viral vectors include Poxviruses; Retroviruses, especially Lentiviruses; Adenoviruses; and Adeno-associated viruses. Viruses have a number of advantages as delivery vehicles, including that they can be tailored to efficiently target certain cell types. Beyond their use as vectors, viruses may also be useful as immunostimulants; and for inducing cell death in cancer cells.

Adenoviruses

The Adenoviruses are a family of DNA viruses infecting mammals, including man. Adenoviral vectors have long been used to transfer DNA into cells of a target organism, and widely used for this purpose. As a result, adenoviral vectors have been used for gene therapy, vaccination, and delivery of therapeutic molecules. Delivery of therapeutic molecules via adenovirus has been shown to be effective in cancer treatment, such as in a rat model of glioma. Ali et al. "Combined immunostimulation and conditional cytotoxic gene therapy provide long-term survival in a large glioma model." *Cancer Res* 65:7194-7204 (2005).

Independently of their use as vectors, Adenoviruses have also been found to be useful in the treatment of cancer. ONYX-015, a gene-attenuated virus causes tumor-specific cytolysis and antitumoral efficacy that can be augmented by standard chemotherapeutic agents. Heise et al. *Nat. Med.* 3(6):639-45 (1997). More specifically, the 55-kilodalton (kDa) protein from the E1B-region of adenovirus binds to and inactivates the p53 gene, which is mutated in half of human cancers. The replication and cytopathogenicity of an E1B, 55-kDa gene-attenuated adenovirus, ONYX-015, is blocked by functional p53 in RKO and U20S carcinoma lines. Normal human cells are highly resistant to ONYX-015-mediated, replication-dependent cytolysis. In contrast, a wide range of human tumor cells, including numerous carcinoma lines are either mutant or normal p53 gene sequences (exons 5-9), were efficiently destroyed. Antitumoral efficacy was documented following intratumoral or intravenous administration of ONYX-015 to nude mouse-human tumor xenografts; efficacy with ONYX-015 plus chemotherapy (cisplatin, 5-fluorouracil) was significantly greater than with either agent alone. Heise et al. *Nat. Med.* 3(6):639-45 (1997).

Further preclinical and clinical studies suggest that cellular stress including heat shock assists in ONYX-015 mediated killing, and that modulation of the proposed molecular mechanism by pharmacologic agents or hyperthermia may largely enhance the therapeutic index of ONYX-015 for tumor cells versus normal tissue and improve clinical efficacy. O'Shea et al, "Heat shock phenocopies E1B-55K late functions and selectively sensitizes refractory tumor cells to ONYX-015 oncolytic viral therapy." Cancer Cell 8, 61-74 (2005); Ries, "Elucidation of the molecular mechanism underlying tumor-selective replication of the oncolytic adenovirus mutant ONYX-015," *Future Oncol.* 6:763-6 (2005).

Based on extensive clinical testing with proven safety and evidence of promising clinical efficacy (Ries, *Future Oncol.* 6:763-6 (2005)) the efficacy of ONYX-015 and related Adenoviruses has been shown in numerous cancers. In 2006, China approved the use of oncolytic virus therapy for cancer treatment. Garber, *J Natl Cancer Inst.* 98:298-300 (2006).

Furthermore, a recent publication has shown that adenoviral delivery of a tumor suppressor gene XAF can antagonize XIAP and sensitize tumor cells to other triggers, causing caspase-independent apoptosis. Qi et al. "Potent antitumor efficacy of XAF1 delivered by conditionally replicative adenovirus vector via caspase-independent apoptosis," *Cancer Gene Ther.* 2006 Sep. 29 [Epub ahead of print].

Accordingly Adenoviruses, including the ONYX-015 adenovirus, may be used to deliver polynucleotides encoding a fusion protein that expresses both an NK-cell stimulatory ligand and an intracytoplasmic DD domain to a tumor cell. The combination of adenovirus infection, NK-cell activation, Fas-mediated apoptosis thereby targets multiple pathways in the cancer cell, leading to cell death. Such therapy may be further enhanced by additional treatments, such as heat shock or chemotherapy, to further induce tumor cell death.

While the ONYX-015 adenovirus replicates preferentially in cancer cells, further specificity may be imparted to narrowly tailor therapy for a given cancer. This may be achieved by engineering viruses to bind only to certain receptors, and by choice of promoters such that fusion protein expression is maximized in cancer, for example.

Preparation of Fusion Polypeptide

Overview

The present invention is not limited to any particular method of producing the fusion protein contemplated herein. According to the contemplated recombinant methods of production, however, the invention provides recombinant DNA constructs comprising one or more of the nucleotide sequences encoding polypeptides, or fragments thereof, described herein. The recombinant constructs of the present invention comprise a vector, such as a plasmid or viral vector, into which a DNA or DNA fragment, typically bearing an open reading frame, is inserted, in either orientation. The invention further contemplates cells containing these vectors.

One of ordinary skill in the art may advantageously use different vectors and host cells for different purposes during construction and screening of fusion proteins. For example, fusion proteins may be cloned in a cloning vector in bacteria under conditions such that the fusion protein is not expressed, such as cloning behind a eukaryotic promoter. When the vector is moved into eukaryotic cells, the fusion protein is expressed. One may similarly modify other elements such as the specificity of the promoter to maximize expression in cancer cells, or control plasmid replication.

Recombinant protein production is well known in the art and is outlined below.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. In a preferred embodiment, the prokaryotic host is *E. coli*.

Bacterial vectors may be, for example, bacteriophage-, plasmid- or cosmid-based. These vectors can comprise a selectable marker and bacterial origin of replication derived from commercially available plasmids typically containing elements of the well known cloning vector pBR322 (ATCC 37017). Such commercial vectors include, for example, GEM 1 (Promega Biotech, Madison, Wis., USA), pBS, phagescript, PsiX174, pBluescript SK, pBs KS, pNH8a, pNH16a, pNH18a, pNH46a (Stratagene); pTrc99A, pKK223-3, pKK233-3, pKK232-8, pDR540, and pRIT5 (Pharmacia). A preferred vector according to the invention is the Pt71 expression vector. Paris et al., *Biotechnol. Appl. Biochem.* 12: 436-449 (1990).

These "backbone" sections are combined with an appropriate promoter and the structural sequence to be expressed. Bacterial promoters include lac, T3, T7, lambda $P_R$ or $P_L$, trp, and ara.

Following transformation of a suitable host strain and growth of the host strain to an appropriate cell density, the selected promoter is derepressed/induced by appropriate means (e.g., temperature shift or chemical induction) and cells are cultured for an additional period. Cells are typically harvested by centrifugation, disrupted by physical or chemical means, and the resulting crude extract retained for further purification.

Eukaryotic Expression

Various mammalian cell culture systems can also be employed to express recombinant protein. Examples of mammalian expression systems include selected mouse L cells, such as thymidine kinase-negative (TK) and adenine phosphoribosyl transferase-negative (APRT) cells. Other examples include the COS-7 lines of monkey kidney fibroblasts, described by Gluzman, *Cell* 23: 175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements.

Mammalian promoters include CMV immediate early, HSV thymidine kinase, early and late SV40, LTRs from retrovirus, and mouse metallothionein-I. Exemplary mammalian vectors include pWLneo, pSV2cat, pOG44, pXT1, pSG (Stratagene) pSVK3, pBPV, pMSG, pcDNA3.1(+,−) (Promega), and pSVL (Pharmacia). Selectable markers include CAT (chloramphenicol transferase).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a target protein in infected hosts. (E.g., See Logan et al., 1984, *Proc. Natl. Acad. Sci. USA* 81: 3655-3659).

Preparation of Nucleic Acids

For in vitro studies, the plasmid that contains the Mult1/Fas fusion protein is transformed into bacteria. Large amount of plasmid DNAs will be prepared from the bacteria. For in vivo studies or therapeutic uses, a virus vector containing the fusion protein is first constructed. This vector together with packaging vector will be transfected into mammalian cells such as 293 cells, from which viral particles containing the fusion protein gene will be harvested and used to introduce the protein into target cells in vivo.

Therapeutic Compositions

The compositions of the invention can be formulated according to known methods to prepare pharmaceutically useful compositions, whereby the inventive molecules, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton Pa. (1980)). In order to form a pharmaceutically acceptable composition suitable for effective administration, such compositions will contain an effective amount of one or more of the polypeptides or polynucleotides of the present invention, and their physiologically acceptable salts and solvates, together with a suitable amount of carrier vehicle.

Pharmaceutical compositions for use in accordance with the present invention may be formulated in conventional manner using one or more physiologically acceptable carriers or excipients, for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release. For buccal administration the composition may take the form of tablets or lozenges formulated in conventional manner.

For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The compositions may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. The compositions may also be formulated for rectal delivery, such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The compositions, since they are useful in cancer treatment, may be formulated in conjunction with conventional chemotherapeutic agents. Conventional chemotherapeutic agents include alkylating agents, antimetabolites, various natural products (e.g., vinca alkaloids, epipodophyllotoxins, antibiotics, and amino acid-depleting enzymes), hormones and hormone antagonists. Specific classes of agents include nitrogen mustards, alkyl sulfonates, nitrosoureas, triazenes, folic acid analogues, pyrimidine analogues, purine analogs, platinum complexes, adrenocortical suppressants, adrenocorticosteroids, progestins, estrogens, antiestrogens and androgens. Some exemplary compounds include cyclophosphamide, chlorambucil, methotrexate, fluorouracil, cytarabine, thioguanine, vinblastine, vincristine, doxorubincin, daunorubicin, mitomycin, cisplatin, hydroxyurea, prednisone, hydroxyprogesterone caproate, medroxyprogesterone, megestrol acetate, diethyl stilbestrol, ethinyl estradiol, tamoxifen, testosterone propionate and fluoxymesterone. In treating breast cancer, for example, tamoxifen is particularly preferred.

Methods of the Invention
Treatment Methods

The therapeutic methods of the invention generally utilize the fusion proteins identified above, nucleic acids encoding such fusion proteins, and compositions thereof. A fusion protein may be delivered to a patient as a polypeptide. Alternatively, a patient may be administered a polynucleotide (for example, as DNA, or packaged in a virus) encoding the fusion polypeptide. Upon uptake of the polynucleotide into the host cell of the patient, the fusion polypeptide is expressed.

Therapeutic methods involve administering to a subject in need of treatment a therapeutically effective amount of a fusion protein or polynucleotide encoding such a fusion protein. "Therapeutically effective amount" is as used herein denotes the amount that is sufficient to slow, inhibit, or reverse cancer growth (e.g., induce apoptosis). Some methods contemplate combination therapy with known cancer medicaments or therapies, for example, chemotherapy (preferably using compounds of the sort listed above) or radiation. The patient may be a human or non-human animal. A patient typically will be in need of treatment when suffering from a cancer characterized by increased levels of receptors that promote cancer maintenance or proliferation.

Administration during in vivo treatment may be by any number of routes, including parenteral and oral, but preferably parenteral. Intracapsular, intravenous, intrathecal, and intraperitoneal routes of administration may be employed. Direct injection into the tumor is advantageous. The skilled artisan will recognize that the route of administration will vary depending on the disorder to be treated.

Determining a therapeutically effective amount of fusion protein, polynucleotide or virus containing such polynucleotide, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (Mack Publishing Company 1990).

Determining a therapeutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the induction or substantial induction of apoptosis in the targeted tissue or a decrease in mass of the targeted tissue. Suitable dosages can be from about 1 ng/kg to 10 mg/kg.

Screening Assays to Determine the Biological Activities of the Fusion Protein

The present invention also provides cell-based assay systems that can be used to compare the biological activities of the cell death/apoptosis-promoting domain, NK activating domain, and/or a fusion protein comprising each of these domains. To this end, a cell proliferation assay is used to ensure that the fused domains of the fusion protein each retain a function similar to the respective domain when it is not fused (i.e. not part of a fusion protein).

In one embodiment, the biological activity of the fusion protein will be determined by introducing the protein to two separate types of cell lines in vitro: each cell line determining the activity of a specific domain. For example, a cell line that is a reliable indicator of the biological activities of the apoptosis-promoting domain should be used to test the effects of that domain, while a cell line capable of indicating NK activation should be used to monitor the activity of the other domain.

By introducing to a cell line various concentrations of a particular domain in its isolated or fused form, one of skill in the art could determine the biological activity of the DD in the fused protein vis-à-vis the same domain in its non-fused state. There are numerous ways to measure apoptosis. These methods include, but are not limited to the following techniques:
(1) Loss of cell viability—measured by a failure to either exclude vital dye or uptake MTT (3-(4,5-dimethylthiazol-2-yl)-2,5-diphenyltetrazolium bromide), or MTS-PMS;
(2) DNA fragmentation—assayed by agarose gel electrophoresis, PFG electrophoresis, in situ terminal transferase labelling (TUNEL);
(3) Cell and nuclear morphology—employing microscopy to visualize chromatin condensation, DNA organization, and cytoplasmic integrity; and
(4) Cysteine protease activation assays—utilizing caspase activation assays combined with colorimetric or fluorescent readouts, poly (ADP-ribose) polymerase (PARP) or laminin cleavage by western blot or immunohistochemistry. Additional assays include Annexin V-FITC staining by FACS and caspase 3 activation by ELISA.

NK activity can be assayed as following. Instead of using Mult1/Fas fusion protein, Mult1 gene alone is used to make a stable cell line expressing Mult1 on their surface. These cells are then used to activate NK cells by co-culture. The activated NK cells will then be used to lyse either Yac-1 cells for mouse or K562 cell for human to determine their killing activity. Other methods of assaying NK activity include stimulation of NK cells with a fusion protein, and assaying NK cells for markers of activation.

Another preferred method for determining activity of the fusion protein according to the invention is the conduct tests in vivo. A suitable host for this test would be a mammalian host containing cancer tissue.

All citations herein are hereby entirely incorporated by reference.

The following examples are intended to be illustrative and not limiting.

EXAMPLES

Example 1

Construction of Vector Encoding Mult1/Fas Fusion Protein, pMULT1E/FasTL

Cloning of MULT1 Extracellular Domain into pcDNA3.1(+)

Thymus glands from 4-day old newborn C57BL/6J mice were removed and stored in liquid nitrogen. The glands were homogenized using a tissue homogenizer and total RNA was extracted using TRIzol reagent (Invitrogen, Carlsbad, Calif.). Primers were designed for amplification of the extracellular domain of MULT1 (Genebank accession # NM_029975) from 236 bp to 868 bp. The sequence of the 5' primer is CCCAAGCTTATGGAGCTGACTGCCAG-TAACAAGGTCC (SEQ ID NO: 5) and that of the 3' primer is CGGGATCCGGTACTGAAAGATCCTGCA GGCTCCAG (SEQ ID NO: 6). At the 5' end of the upstream primer, a Hind III enzyme site was created and at the 5' end of downstream primer, a BamH I site was created. cDNA was synthesized from the extracted total RNA using RT-PCR kit (Promega, Madison, Wis.). The fragment was excised and gel purified using a Qiagen gel purification kit (Valencia, Calif.).

Double enzyme digestion was performed on the purified fragment using Hind III and BamH I. The enzyme digested fragment was then ligated into a pcDNA3.1(+) vector (Invitrogen, CA). The full extracellular MULT1 cDNA sequence in the new vector, pMULT1E, was confirmed by DNA sequencing.

Cloning of Fas Transmembrane and Intracellular Domains into pcDNA3.1(+)/Zeo

The cDNA clone of the Fas receptor in pDNR-LIB (ATCC #10088798) was purchased from American Type Collection Centre (ATCC, Manassas, Va.). A pair of primers were designed for amplification of the transmembrane and intracellular domains of Fas from 524 bp to 1013 bp (Genebank accession # BC061160). The 5' primer used was CGGGATC-CCCCAGAAATCGCCTATGGTTGTTGTTGACC (SEQ ID NO: 7) and the 3' primer was CGGAATTCTCACTCCA-GACATTGTCCT TCATTTTC (SEQ ID NO: 8). At the 5' end of upstream primer, a BamH I enzyme site was created and at the 5' end of downstream primer, an EcoR I enzyme site was created. DNA PCR was performed to amplify the Fas transmembrane and intracellular domains from pDNR-LIB. The gel purified fragment was treated with BamH I and EcoR I enzymes and ligated into the pcDNA3.1(+) vector to create pFasTI. The DNA sequence of the transmembrane and intracellular domains of Fas in vector pFasTI was confirmed by DNA sequencing.

Creation of the Vector pMULT1 E/FasTI

Figure 1:
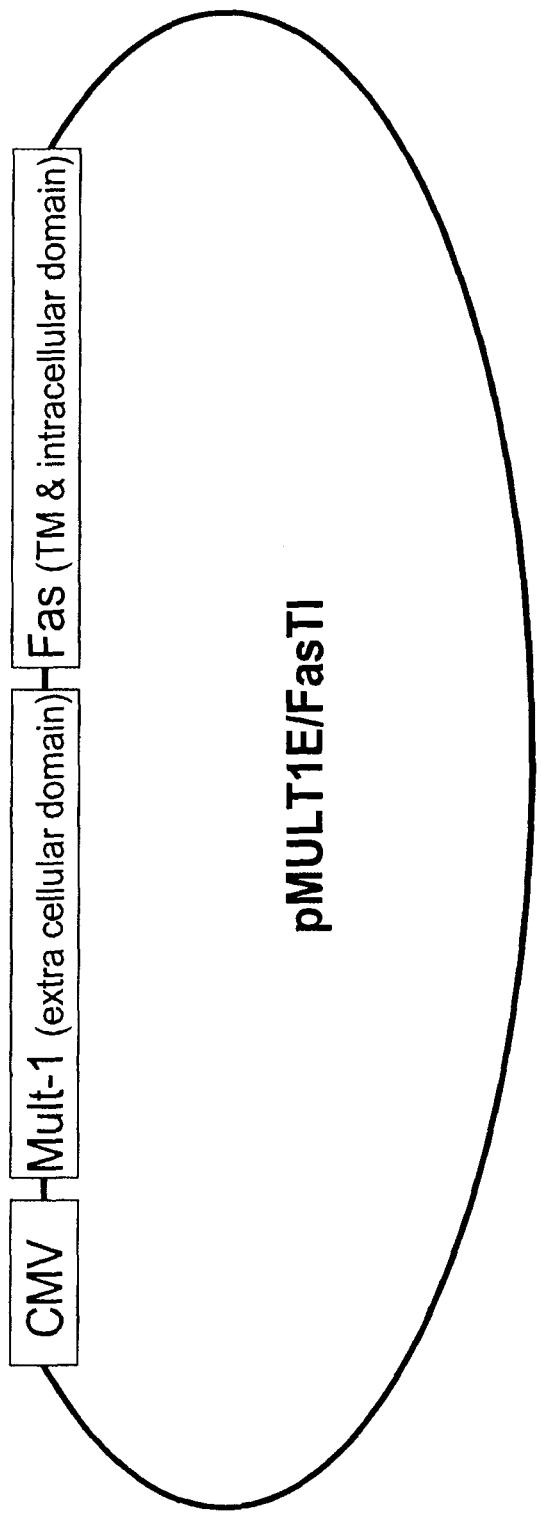
FIG. 1. Construction of the plasmid. The extra cellular domain of mouse Mult1 cDNA ("Mult1E) and the transmembrane (TM) and intracellular domains of mouse Fas cDNA ("FasTI") were cloned by PCR, respectively. The two pieces of cDNAs in the order of Mult1/Fas were inserted into plasmid pcDNA3.1/Zeo, to generate pMULT1E/FasTI.

The cDNA fragment encoding the MULT1 extracellular domain was cut out from pMULT1E by Hind III and Bam HI enzyme digestion and ligated into the pFasTI. The resulting vector was named pMULT1E/FasTI (FIG. 1) and used for transfection.

Example 2

Transfection of TC-1 Tumor Cells with Vector Encoding Mult1/Fas, and Expression

Materials and Methods

Mice and Cells

C57BL/6J mice (male or female) at 6-8 weeks of age were purchased from Jackson Laboratories (Bar Harbor, Me.) and housed in our pathogen-free animal facilities. The animal experiments were carried out in accordance with the Guidelines for the Care and Use of Laboratory Animals (NIH Publication Number 85-23) and the institutional guidelines. The mouse lung carcinoma cell line TC1 (ATCC # JHU-1) was cultured in RPMI 1640 medium containing 10% FBS and 100 µg/ml gentamicin at 37° C. with 5% $CO_2$.

Transfection of TC-1 Cells

TC-1 mouse lung carcinoma cells were transfected with linearized pMULT1E/FasTI vector using Lipofectamine (Invitrogen, Carlsbad, Calif.) as directed by the manufacturer. In order to obtain stable clones expressing the fusion protein, the transfected cells were cultured in medium containing 250 µg/ml zeocin. Zeocin resistant clones were obtained and subcultured in the presence of zeocin.

Fusion Protein Expression by Transfected TC-1 Clones

Figure 2A:
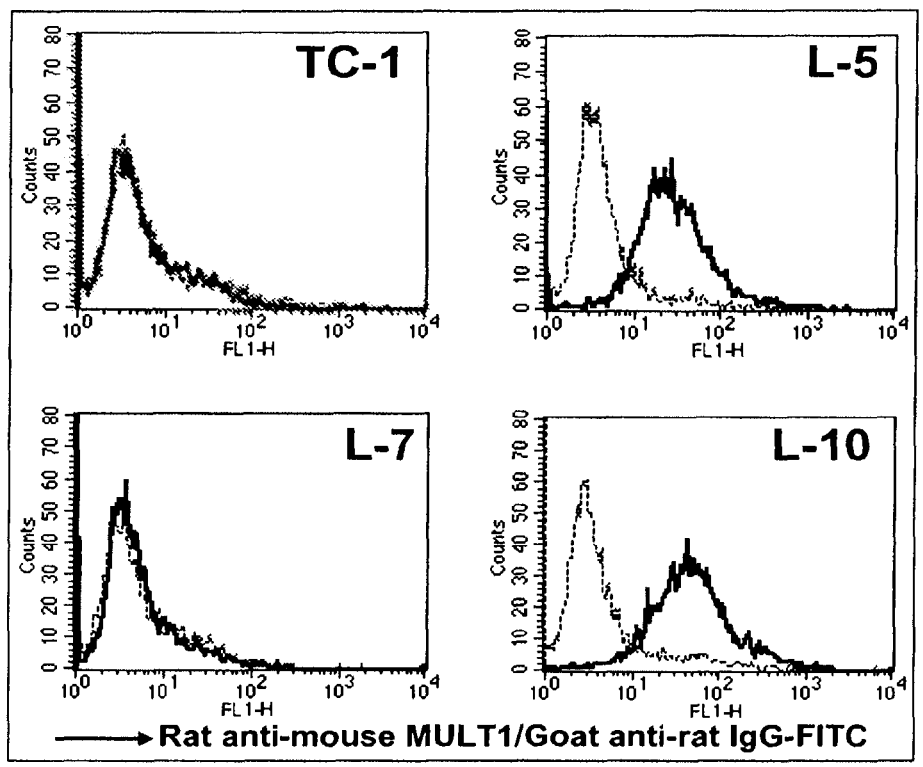
FIGS. 2A-E. FACS and RT-PCR analyses of MULT1E/FasTI expression.

For the analysis of MULT1 E/FasTI surface expression, cells from TC-1 or zeocin-resistant clones were gently detached using TrypLE Express (Invitrogen) and washed with staining buffer twice. $5 \times 10^5$ cells of each clone were incubated with 1 µg monoclonal rat anti-mouse MULT1 antibody (R&D Systems, Minneapolis, Minn.) for 30 minutes at 4° C. After washing twice with staining buffer, the cells were stained with FITC-labeled goat F(ab'), anti rat IgG antibody for 30 minutes at 4° C. After washing twice with staining buffer, cells were re-suspended in 0.5 ml staining buffer and analyzed on FACS Calibur (Becton Dickinson, San Jose, Calif.) using CellQuest software (Becton Dickinson, San Jose, Calif.). To confirm that MULT1E expressed as the fusion protein in the transfected cells can indeed bind to NKG2D, cells were first treated with 1 µg/ml of NKG2D/Fc, a recombinant protein of mouse NKG2D (R&D Systems) for 30 min at RT, stained with FITC-labeled rat anti-mouse NKG2D antibody, and analyzed by FACS. As response of host to tumors typically depends on the level of NKG2DL expressed on tumors, three clones of cells were chosen for this study: clone L7 expressing low levels of MULT1E/TI, clones L5 and L10 expressing high levels of MULT1E/FasTI and, as a control, cell line TC-1 expressing very low levels of endogenous MULT1 (FIG. 2A).

RT-PCR

Two million cells of TC1, L-5, L-7 and L10 were used to extract total RNA using TRIzol reagent (Invitrogen, Carlsbad, Calif.). RNA samples were DNase 1 treated prior to reverse transcription using RQ1 RNase free DNase ((Promega, Madison, Wis.). The treated RNAs were then used for RT-PCR using Access Quick™ RT-PCR system (Promega, Madison, Wis.) according to the manufacture's protocol. Two different RT-PCR reactions were performed. The first for amplifying only MULT1 extracellular fragment using MULT1 forward and reverse primers 5' CCCAAGCT-TATGGAGCTGACTGCCAGTAACAAGGTCC 3' (SEQ ID NO: 5) and 5'CGGGATCCGGTACTGAAAGATCCTG-CAGGCTCCAG 3'(SEQ ID NO: 6). The second for amplifying the complete MULT1-Fas fusion protein mRNA with MULT1 forward and Fas reverse primers: 5' CCCAAGCT-TATGGAGCTGACTGCCAGTAACAAGGTCC 3'(SEQ ID NO: 5) and 5'CGGAATTCTCACTCCAGACATTGTCCT-TCATTTTC 3'(SEQ ID NO: 8). RT-PCR for β-actin was also performed as control.

Induction of Apoptosis in Cells Expressing the Fusion Protein

To determine if cells expressing the fusion protein can be induced to undergo apoptosis, $1 \times 10^6$ cells of TC-1 or clones L5, L7 or L10, were treated with 1 µg/ml of NKG2D/Fc for 16 hrs. The apoptosis of the cells were measured using two systems: a TACS Annexin V-FITC apoptosis kit (R&D Systems) and a caspase-3 fluorometric assay (R&D Systems). For the Annexin-V assay, $2 \times 10^5$ cells in triplicate were stained according to the instructions provided by the manufacturer. Briefly, cells were trypsinized, washed twice with staining buffer, and incubated with Annexin V-FITC and PI in binding buffer at room temperature for 15 min in the dark. Stained cells were analyzed by FACS. For caspase-3 analysis, $8 \times 10^5$ cells in triplicates were used for analysis of caspase-3 activity according to the instructions provided by the manufacturer. Briefly, cells were trypsinized, washed with PBS, lysed. The lysates were incubated with caspase-3 substrate for 1 hour at 37° C. and the fluorescent signal was detected using a SpectraMax Gemini XS microplate reader (Molecular Devices, Sunnyvale, Calif.).

Activation of NK Cells by MULT1E/FasTI

To test whether the MULT1E/FasTI fusion protein can activate NK cells, $1 \times 10^6$ cells of TC-1 and clones L-5, L-7, and L-10 were co-cultured for three hours at a ratio of 1:2 with NK cells isolated from the spleens of female C57BL/6J mice using a mouse NK cell isolation kit (Miltenyi Biotec, Auburn, Calif.). The NK cells were then recovered and stained with anti-mouse NK1.1 antibody conjugated with FITC (BD Biosciences, San Diego, Calif.). The cells were then permeabilized and fixed using the Cytofix/Cytoperm Plus (BD Biosciences), stained with anti-mouse interferon-γ antibody-PE (BD Biosciences) and analyzed by FACS using the CellQuest software for intracellular IFN-γ production.

Statistical Analysis

GraphPad software (Prism, San Diego, Calif.) was used to make graphs. One-way or Two-way ANOVA with Bonferoni post-tests were used to perform the statistical analyses of the data. Student t test was used to analyze the subcutaneous tumor growth data (FIG. 5). The significance was represented as $p<0.05$, *; $p<0.01$, ; $p<0.001$, *.

Results

Expression of MULT1E/FasTI

Figure 2B:
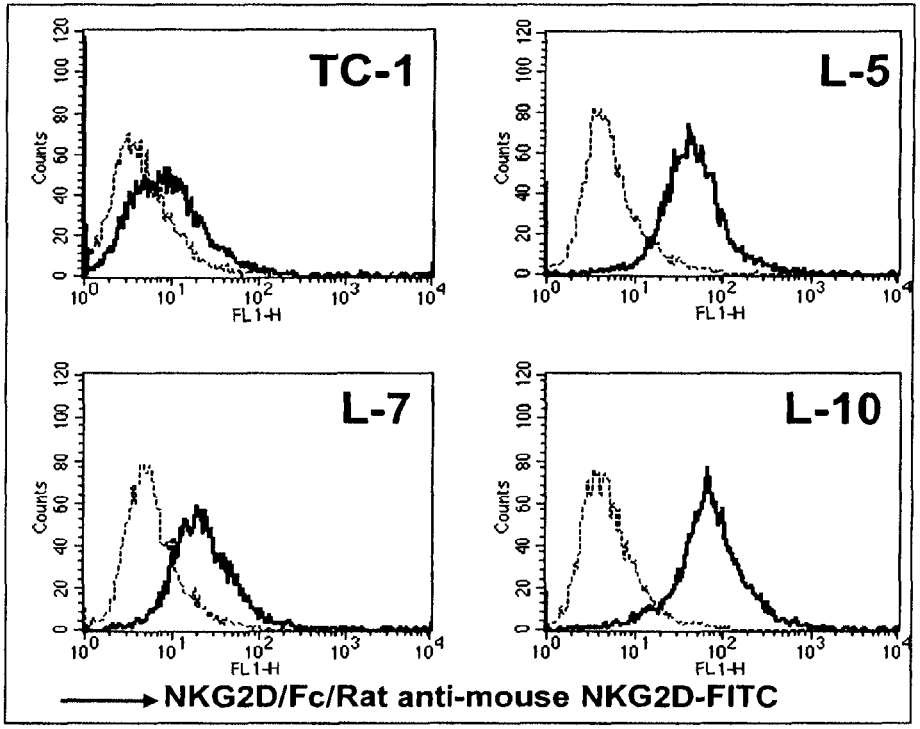

TC-1 cells were transfected with pMULT1E/FasTI. Clones that were zeocin resistant were selected. The cells of these clones were stained with anti-mouse MULT1 antibody and analyzed by FACS. The result shows that TC-1 cells and clone L7 cells were negative, while clones L5 and L10 cells were strong positive for expression of MULT1E/FasT1 on their surface (FIG. 2A). In order to confirm that MULT1E of the fusion protein can indeed bind to NKG2D, the cells were treated with NKG2D/Fc and then stained with anti-mouse NKG2D antibody conjugated with FITC. TC-1 cells and clone L-7 cells are dimly positive, while clones L-5 and L-10 cells are strongly positive (FIG. 2B) with L-10 cells the strongest.

Effect of Mult1/Fas Clone on Tumor Cell Growth

Figure 2C:
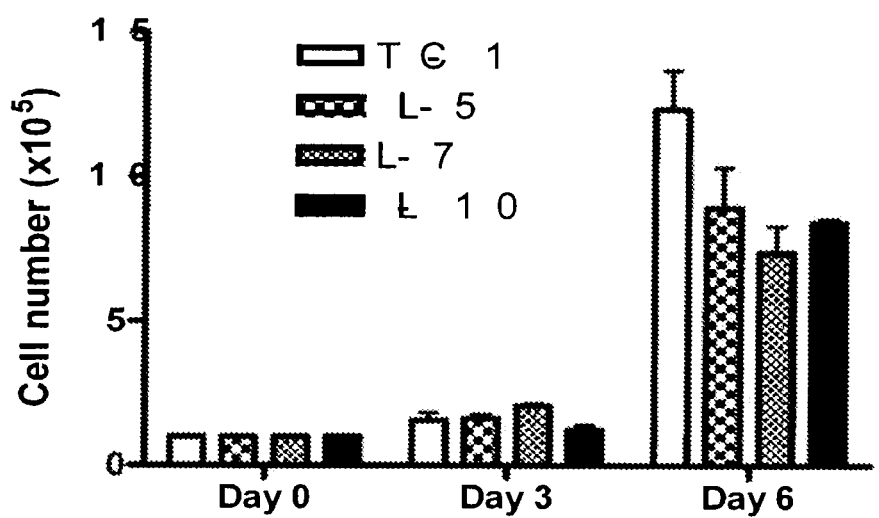

FIG. 2C shows in vitro tumor growth. $1 \times 10^5$ tumor cells of TC-1 or clones L-5, L-7 or L-10 were inoculated in culture wells and cultured. The numbers of cells in each well were counted after 3 and 6 days of culture. At day 3, there were no significant difference among these clones. At day 6, the number of TC-1 tumor cells were significantly higher than that of the other clones. However, there was no significant difference among clones L-5, L-7, and L-10.

RT-PCR Confirms Expression of Fusion Protein

Figure 2D:
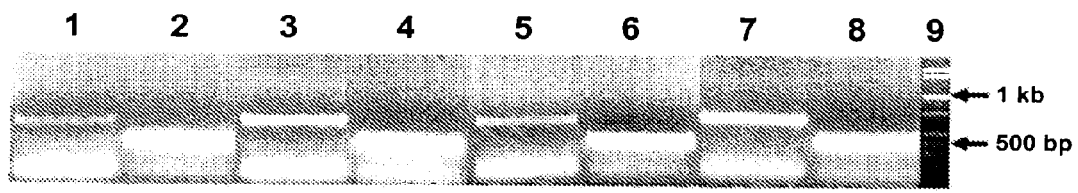
Figure 2E:
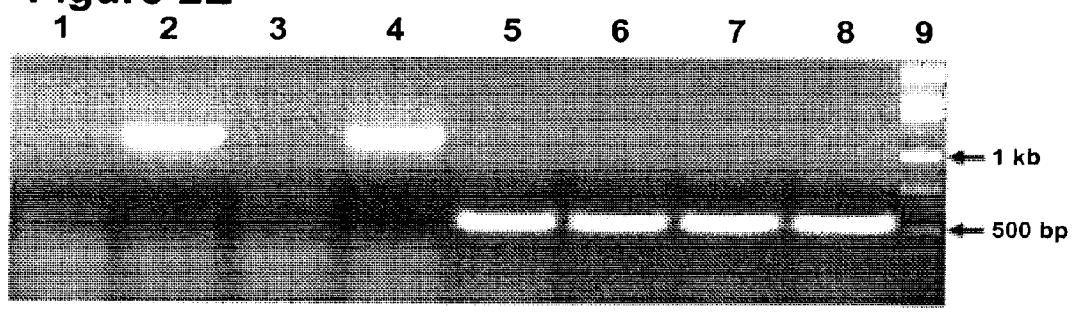

In order to further confirm the fusion protein expression, RT-PCR was performed on RNA samples from these clones using two pairs of primers: the first pair covers only the extracellular domain of MULT1; while the second pair covers the entire fusion protein. As FIG. 2D shows, although all the clones are positive for the first pair of primer (646 bp), signals of clones L-5 and L-10 are much stronger than those of TC-1 cells and clone L-7. Only clones L-5 and L-10 are positive for the second pair of primer (1134 bp, FIG. 2E). The results indicate that clones L-5 and L-10 are MULT1E/FasTI positive clones, while TC-1 and clone L-7 are negative for the fusion protein, but express some endogenous MULT1 protein.

Fusion Protein MULT1E/FasTI Induces Apoptosis of Cells

To confirm that, when bound by its ligand, fusion protein MULT1E/FasTI can send death signals into cells, TC-1 cells and clones L-5, L-7, L10 were treated with recombinant protein NKG2D/Fc and analyzed by Annexin-V staining and caspase-3 activation assay. The treatment of NKG2D/Fc increases both Annexin-V positive cells and Annexin-V/PI double positive cells in clones L-5 and L-10, but not in TC-1 cells or clone L-7 (FIG. 3A). After the NKG2D/Fc treatment, not only apoptotic cells (Annexin-V positive cells and Annexin-V/PI double positive cells), but also the necrotic cells (PI positive/Annexin V negative cells) in clone L-5 and L-10 are significantly higher than those of TC-1 or clone L-7 (FIGS. 3B and 3C). Similarly, caspase-3 activities in cells of clones L-5 and L-10 are significantly higher than those of TC-1 or clone L-7 (FIG. 3D). The treatment of NKG2D/Fc induced more apoptotic cells in clone L-10 than clone L-5 (FIGS. 3B and 3D).

Cells Expressing MULT1E/FasTI Activate NK Cells

To determine whether fusion protein MULT1E/FasTI can also activate NK cells, cells from TC-1 or clones L-5, L-7, or L-10 were co-cultured with NK cells isolated from mouse spleen. Intracellular IFN-γ was detected by FACS analysis (FIG. 4A). The percentage of the NK cells that express IFN-γ are significantly increased in wells that contained cells of clone L-5 or L-10 compared to those co-cultured with TC-1 (p<0.05). While the percentage of NK cells expressing IFN-γ in wells that contained cells of clone L-7 increased slightly compared to those co-cultured with TC-1 cells, it is not statistically significant (FIG. 4B).

This in vitro cell cultured study therefore demonstrated that NKG2D/Fc, a recombinant protein of mouse NK cell receptor NKG2D, was able to elicit the apoptosis process through the Fas transmembrane and intracellular domains of MULT1-Fas in cells expressing the fusion protein as assayed by Annexin V-FITC staining and caspase-3 ELISA, and was able to stimulate NK cells.

Example 3

In Vivo Studies in Mice Injected with Tumor Cells

Materials and Methods

Female C57BL/6J mice at 6-8 weeks of age were used in two tumor model studies: a subcutaneous tumor model and a pulmonary metastasis model with cells of TC-1 or clones L5, L7 or L10. For the subcutaneous study, $2 \times 10^5$ cells of the above clones in 0.2 ml HBSS were injected subcutaneously in the right flank of each of the 4 animals. Tumors were measured twice weekly. Tumor size was calculated as $1/2LW^2$, where W and L are the shortest and longest diameters of the tumor, respectively. For pulmonary metastasis studies, $2 \times 10^5$ cells in 0.5 ml of HBSS were injected intravenously. Four weeks after tumor injection, the mice were euthanized and their lungs were excised. The tumor nodules on each lung were counted using a dissecting microscope, tumor weight was also determined by weighing the lungs.

In Vivo Anti-Tumor Effect of Fusion Protein MULT1E/FasTI

The in vivo therapeutic effect of the fusion protein was evaluated in a subcutaneous tumor model as well as a pulmonary metastasis model. Two hundred thousand cells of TC-1 and clones L-5, L-7, and L-10 in 0.2 ml HBSS were injected subcutaneously into 6-8 week old mice and tumor size was measured twice weekly with caliper and tumor volume was calculated. The tumor growth of clone L-7 is slightly, but not significantly (p>0.05) slower when compared to that of TC-1 cells. At day 18, the growth of clones L-5 and L-10 are significantly slower (p<0.01, p<0.01) when compared to that of TC-1 cells. At day 24, the difference of tumor growth between TC-1 and clone L-10 is even more significant (p<0.001), while the difference of tumor growth between TC-1 and clone L-5 remains the same (p<0.01, FIG. 5). An even better anti-tumor effect of the fusion protein was observed in the pulmonary metastasis model. Four weeks after intravenous tumor cells injection, the mice were euthanized and lungs were excised (FIG. 6A). The total weight of the lungs with the tumors were measured (FIG. 6B) and the tumor nodules on the surface of the lungs were counted (FIG. 6C). The lungs isolated from mice injected with TC-1 cells are fully covered with tumors and weigh an average 0.82 grams. All the four lungs have more than 200 tumor nodules each. The lungs isolated from mice injected with clone L-7 cells are covered with many tumors as well and weigh averagely 0.48 grams. There are 118, 89, 67, 125 tumor nodules on the lungs. The lungs isolated from mice injected with clones L-5 and L-10 are almost tumor free and weigh much less (0.15 grams and 0.14 grams, respectively) than those of mice injected with either TC-1 cells or clone L-7 cells. The average weight of lungs from normal mice is 0.14 grams.

In conclusion, a bifunctional chimeric protein containing the extracellular domain of MULT1 and the transmembrane and intracellular domains of Fas was created. Both in vitro and in vivo studies demonstrated its antitumor activity.

Example 4

In Vivo Delivery of Mult1/Fas

An adenovirus vector containing Mult1/Fas cDNA is constructed and transfected into mammalian cells. Viral particles are produced, and harvested. The viral vectors are then injected directing into tumors on mice to determine that the fusion protein can be efficiently expressed by the tumor cells and that the tumor cells are be eradicated.

Example 5

Human Treatment

An adenovirus vector containing Mult1/Fas cDNA is constructed and transfected into mammalian cells. Viral particles are produced, and harvested. The viral vectors are then injected directing into human tumors. The fusion protein is expressed and cell killing is effected both via apoptosis and NK-cell activation. Tumor regression is observed by decreased tumor mass.

The invention claimed is:

1. A polynucleotide encoding the polypeptide comprising (i) a ligand for a stimulatory Natural Killer (NK) receptor and (ii) an intracytoplasmic death domain (DD), wherein the polynucleotide comprising nucleotides 7 to 1134 of SEQ ID NO: 4.

2. A polynucleotide comprising the polynucleotide of claim 1, operatively linked to a promoter.

3. The polynucleotide of claim 2, wherein said promoter is activated in cancer.

4. A method of promoting NK-mediated killing of a target cell comprising delivering the polynucleotide of claim 1, to said target cell.

5. A method of treating cancer, comprising administering the polynucleotide of claim 1, to a cancer cell.

6. The method of claim 5, wherein said polynucleotide is administered directly to a tumor.

7. The method of claim 6, wherein said polynucleotide is administered via an adenovirus.

8. A composition comprising the polynucleotide of claim 1, and a pharmaceutically acceptable excipient.

9. A viral particle, comprising the polynucleotide of claim 1.

* * * * *